US008608800B2

(12) United States Patent
Portney

(10) Patent No.: US 8,608,800 B2
(45) Date of Patent: Dec. 17, 2013

(54) SWITCHABLE DIFFRACTIVE ACCOMMODATING LENS

(76) Inventor: Valdemar Portney, Newport Coast, CA (US)

( * ) Notice: Subject to any disclaimer, the term of this patent is extended or adjusted under 35 U.S.C. 154(b) by 0 days.

(21) Appl. No.: 13/247,840

(22) Filed: Sep. 28, 2011

(65) Prior Publication Data

US 2013/0035760 A1    Feb. 7, 2013

Related U.S. Application Data

(60) Provisional application No. 61/514,413, filed on Aug. 2, 2011.

(51) Int. Cl.
*A61F 2/16* (2006.01)

(52) U.S. Cl.
USPC ......... 623/6.37; 623/6.13; 623/6.3; 623/6.31; 351/159.11

(58) Field of Classification Search
USPC .............. 623/6.37, 6.13, 6.22, 6.3, 6.31; 351/159.04, 159.18, 159.61, 159.11, 351/159.15, 159.35, 159.44
See application file for complete search history.

(56) References Cited

U.S. PATENT DOCUMENTS

| | | | | |
|---|---|---|---|---|
| 4,564,267 | A | | 1/1986 | Nishimoto |
| 4,601,545 | A | * | 7/1986 | Kern ............................ 349/200 |
| 4,892,543 | A | * | 1/1990 | Turley .......................... 623/6.13 |
| 5,476,514 | A | | 12/1995 | Cumming |
| 6,730,123 | B1 | * | 5/2004 | Klopotek ..................... 623/6.22 |
| 7,452,378 | B2 | | 11/2008 | Zadno-Azizi et al. |
| 2002/0188351 | A1 | * | 12/2002 | Laguette ...................... 623/6.24 |
| 2003/0060878 | A1 | * | 3/2003 | Shadduck ................... 623/6.13 |
| 2004/0169816 | A1 | * | 9/2004 | Esch .......................... 351/160 R |
| 2007/0032866 | A1 | | 2/2007 | Portney |
| 2007/0168027 | A1 | * | 7/2007 | Brady et al. ................. 623/6.31 |
| 2008/0180630 | A1 | * | 7/2008 | Clarke et al. ................. 349/201 |
| 2008/0208335 | A1 | * | 8/2008 | Blum et al. .................. 623/6.22 |
| 2009/0256977 | A1 | | 10/2009 | Haddock et al. |
| 2010/0066973 | A1 | | 3/2010 | Portney |
| 2010/0179653 | A1 | * | 7/2010 | Argento et al. ............. 623/6.13 |
| 2011/0176103 | A1 | | 7/2011 | Iyer et al. |

FOREIGN PATENT DOCUMENTS

WO    WO 2011/092169 A1    8/2011
WO    WO 2011/163668 A2 *  12/2011

OTHER PUBLICATIONS

Fujita T and Idesawa M, "Accommodation Assisted Glasses for Presbyopia", Proceedings of the SPIE, 2002;4902:99-109 (Oct. 2002).
Kern SP, "Bifocal, electrically switched intraocular and eyeglass molecular lenses" Proceedings of the SPIE, 1986;601:155-158 (May 1986).
Li G, Mathine DL, Valley P, et al. "Switchable electro-optic diffractive lens with high efficiency for ophthalmic application", Proceedings of the National Academy of Science of the USA, 2006; 103: 6100-6104 (Apr. 2006).

* cited by examiner

*Primary Examiner* — Paul Prebilic
(74) *Attorney, Agent, or Firm* — Hackler Daghighian & Martino

(57) ABSTRACT

A lens in accordance with the present invention includes an accommodating cell having two chambers with at least one chamber filled with optical fluid with the refractive index matching the refractive index of the accommodating element separating them. The accommodating element has a diffractive surface with surface relief structure that maintains its period but changes its height due a pressure difference between the chambers to redirect most of light that passes through the lens between different foci of far and near vision. The invention also includes a sensor cell that directly interacts with the ciliary muscle contraction and relaxation to create changes in pressure between the accommodating cell chambers that results in changing surface relief structure height and the lens accommodation.

6 Claims, 13 Drawing Sheets

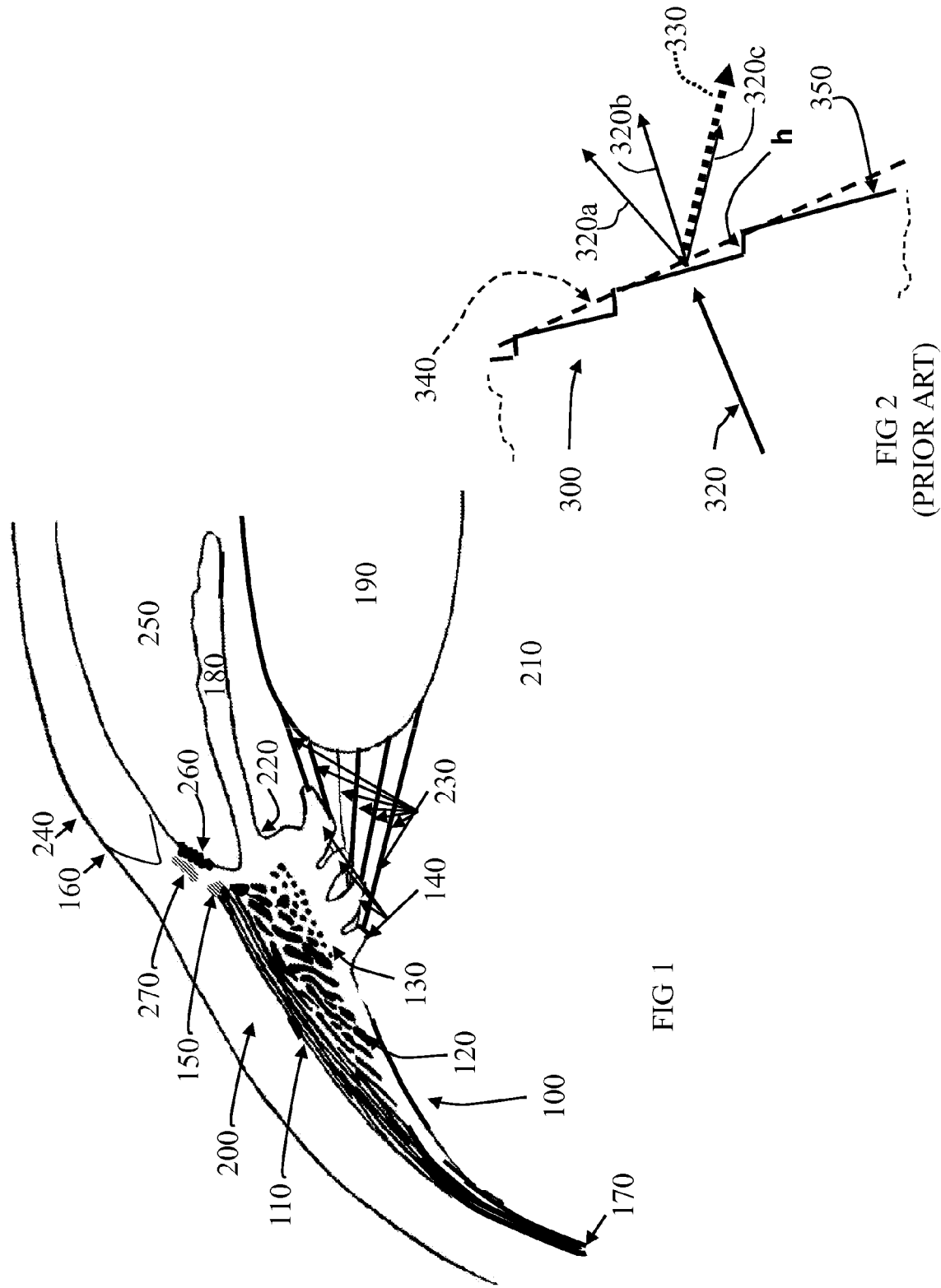

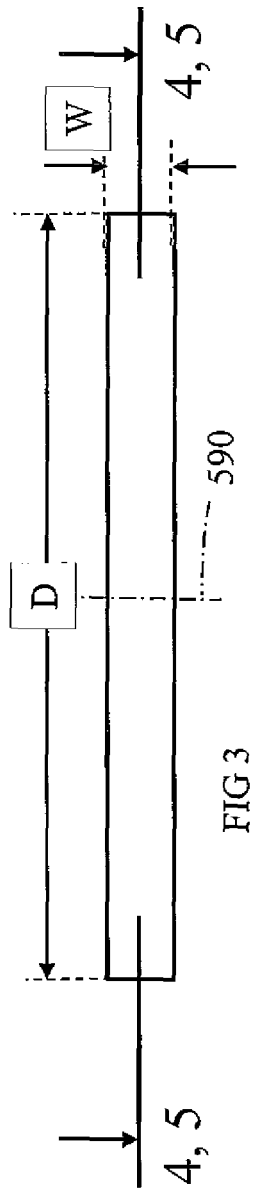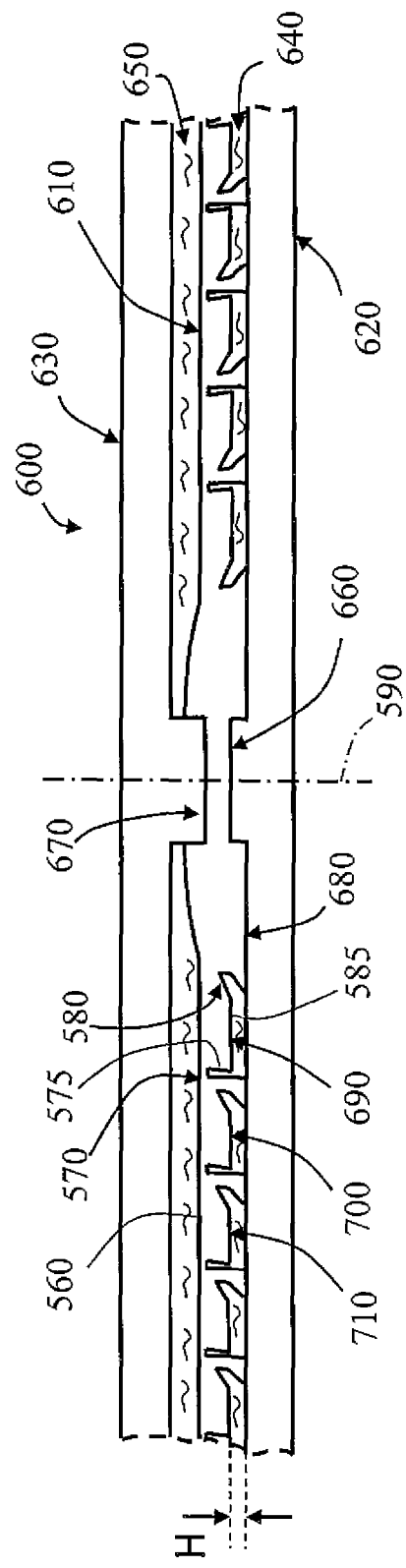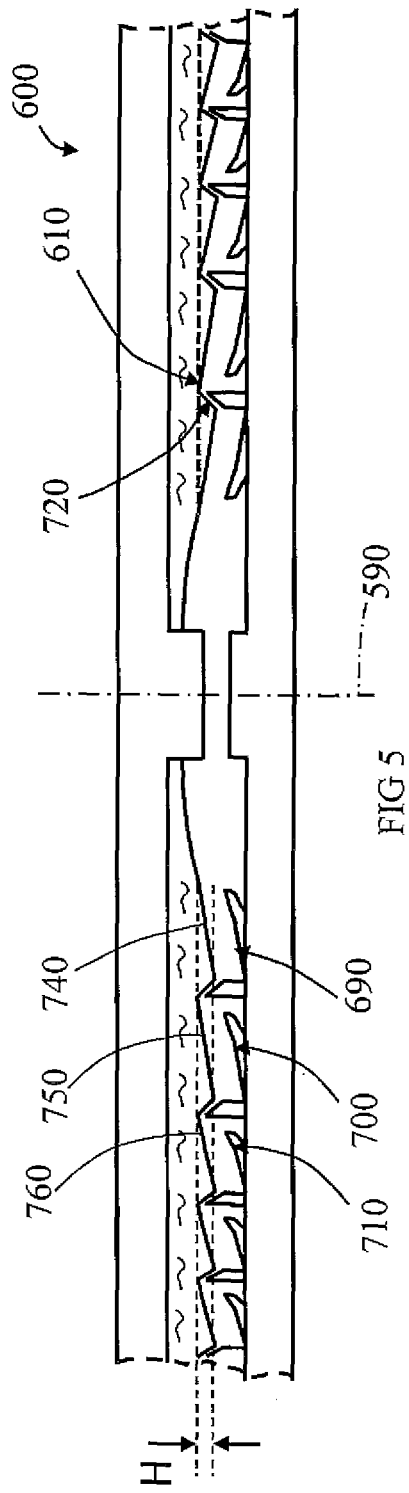

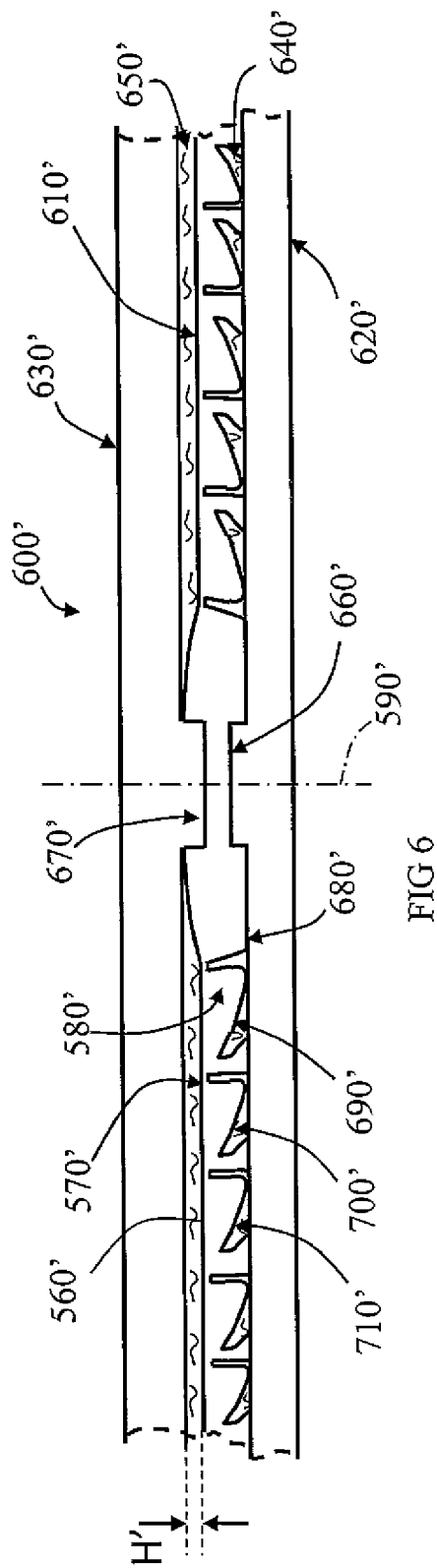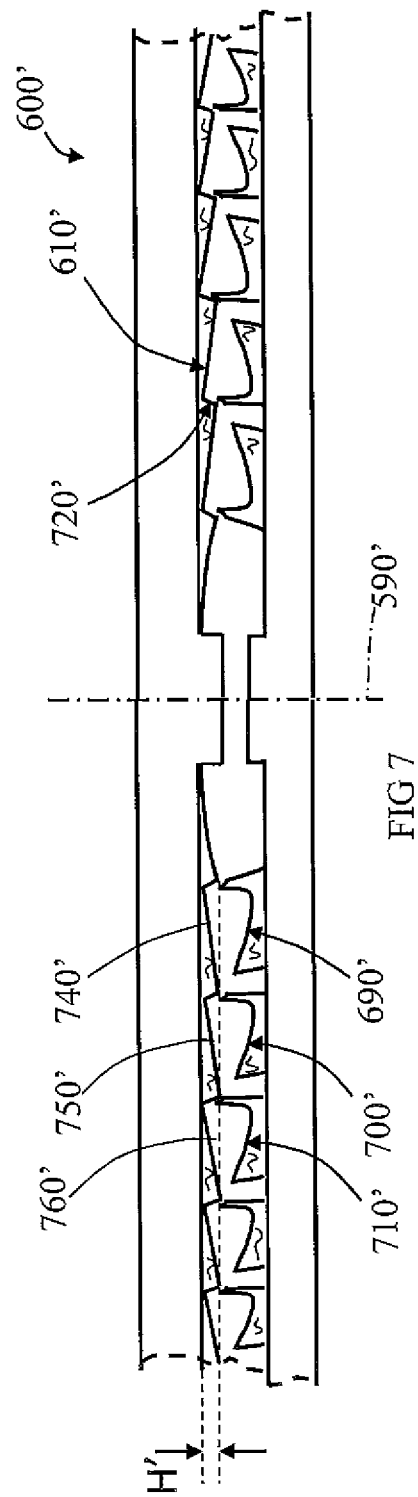

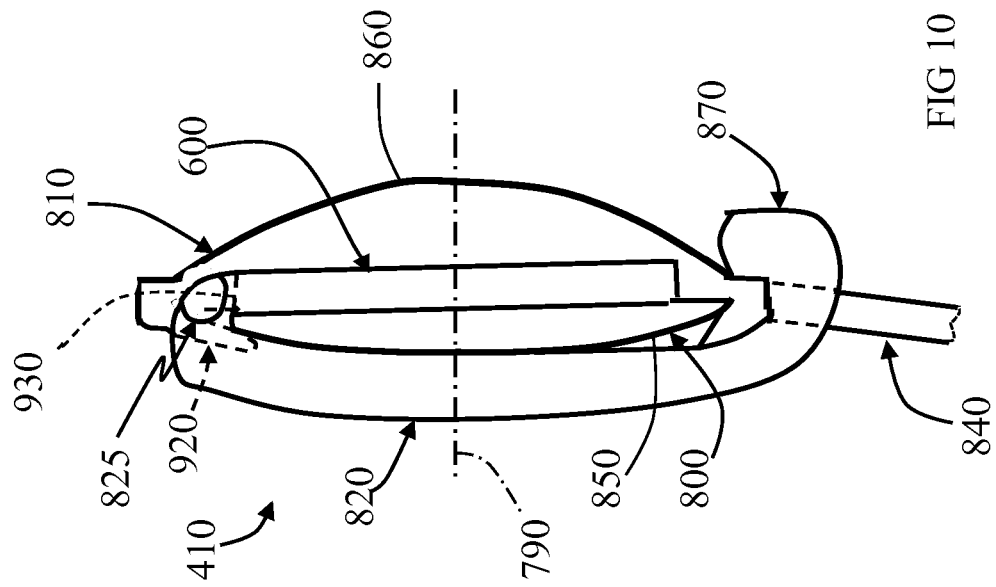
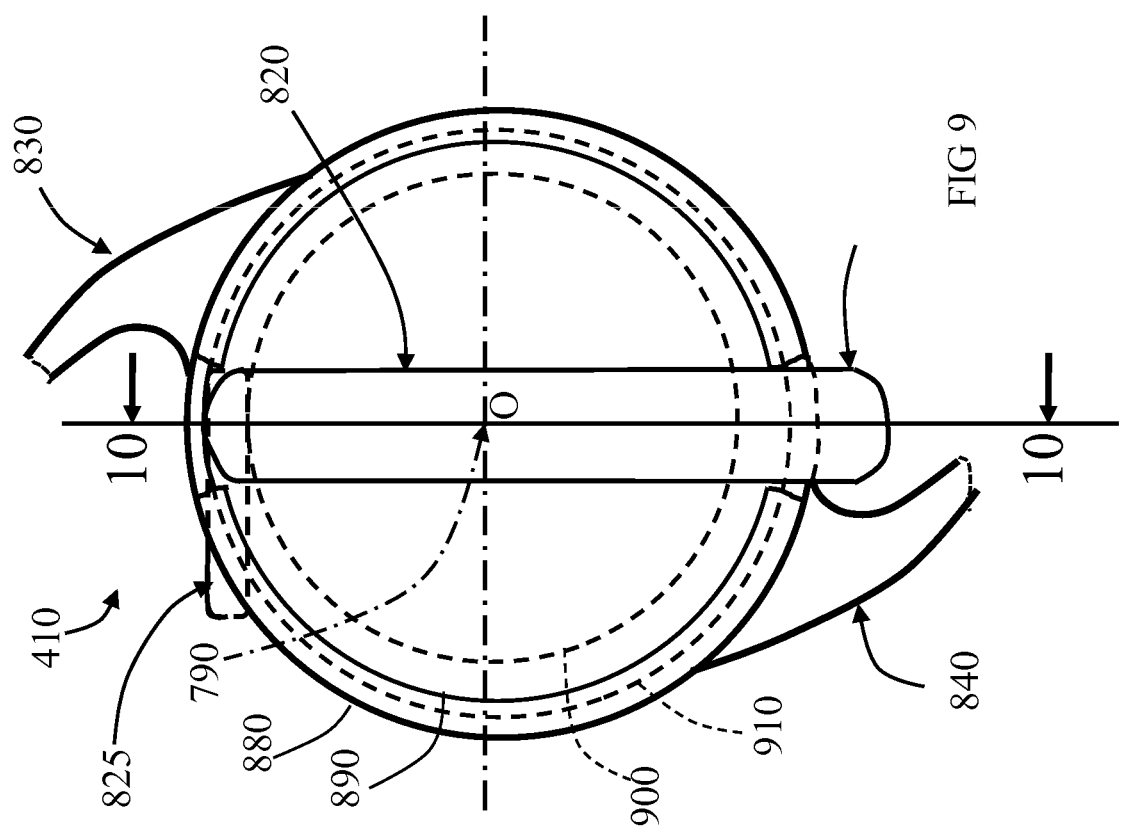

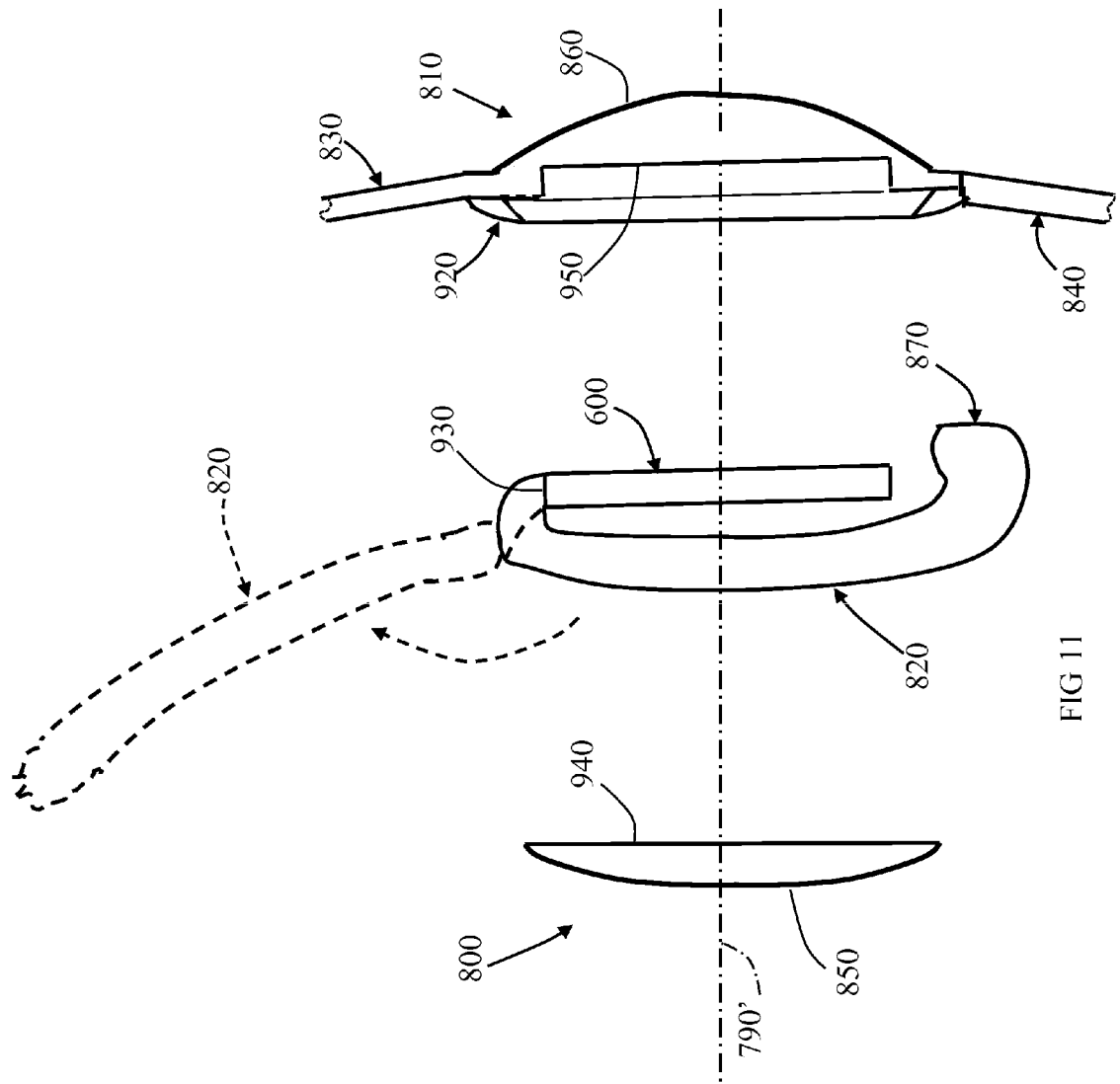

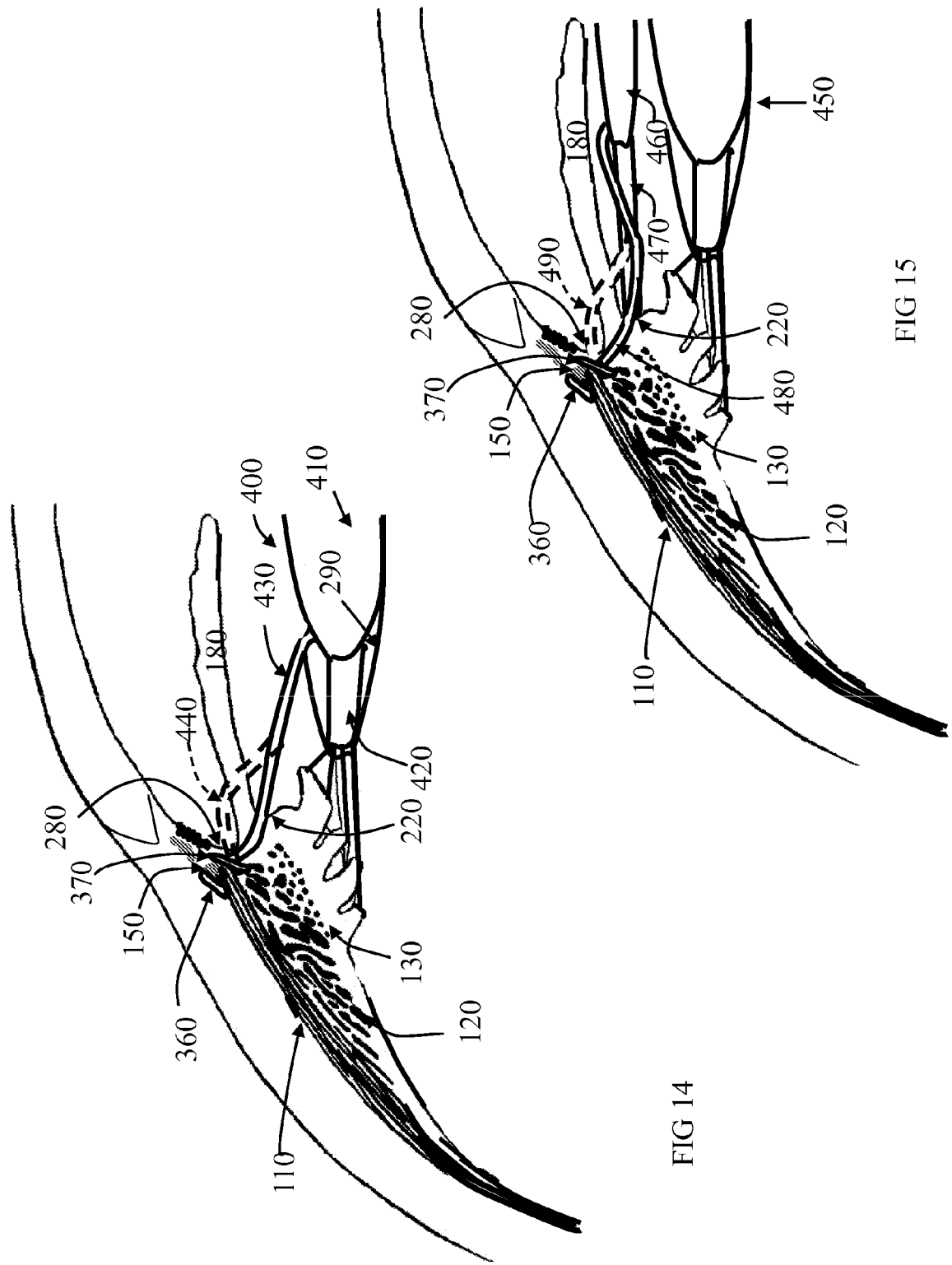

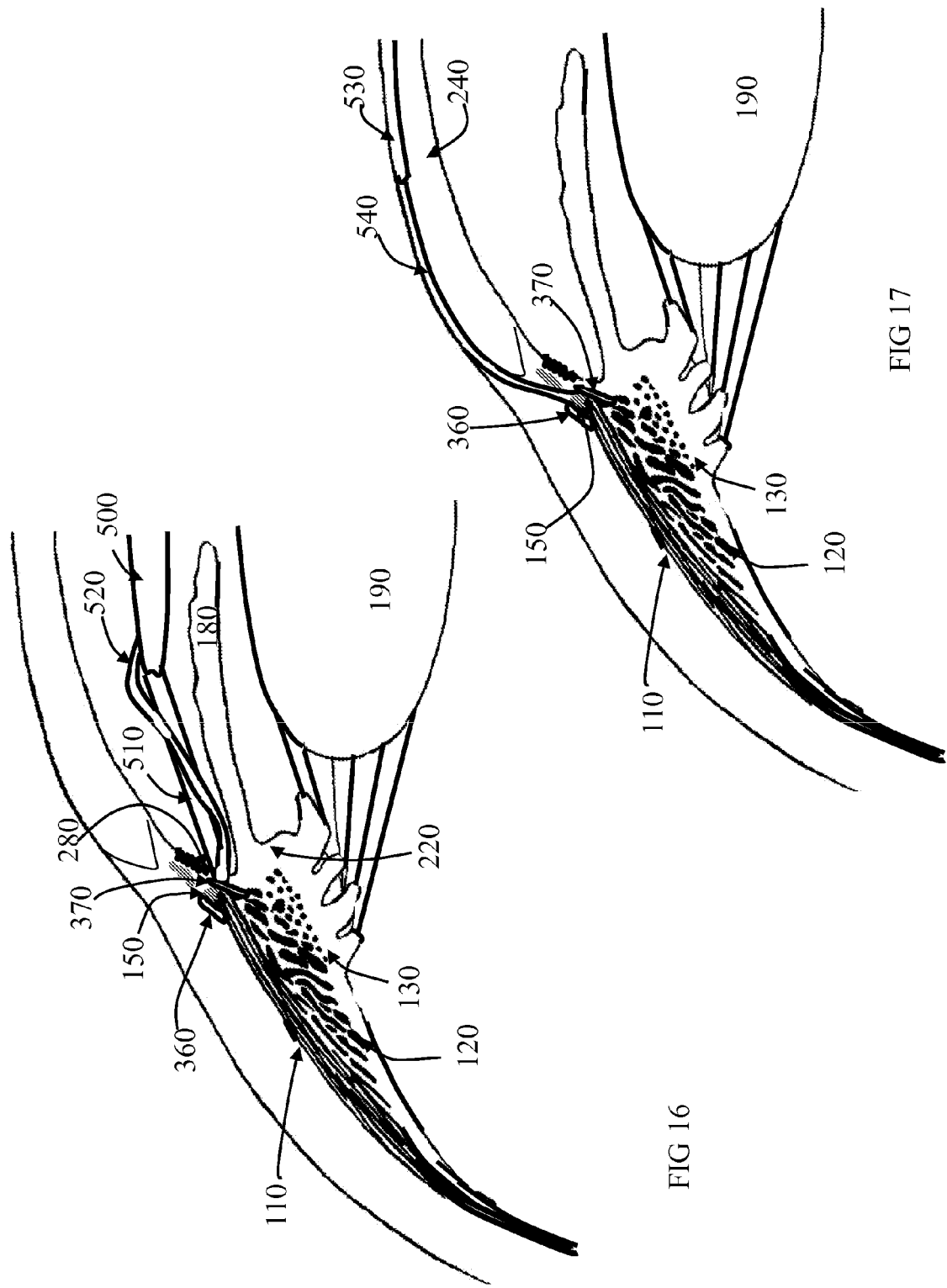

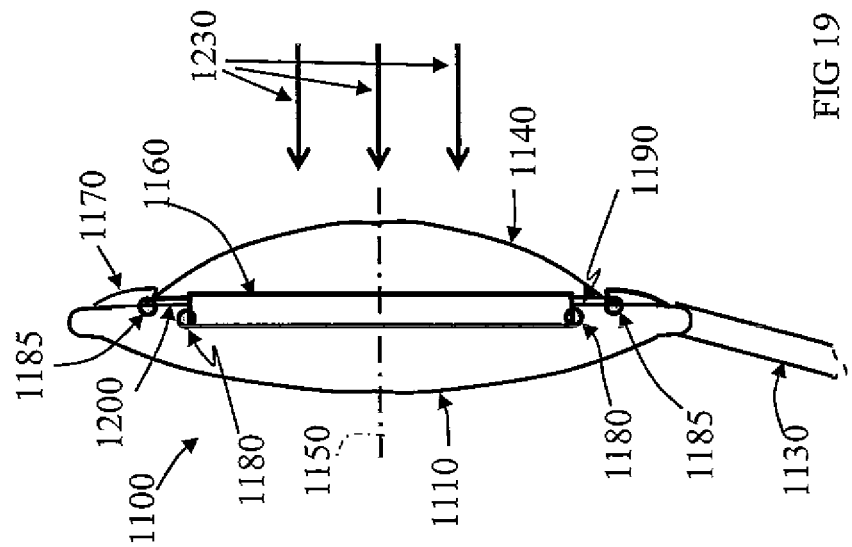
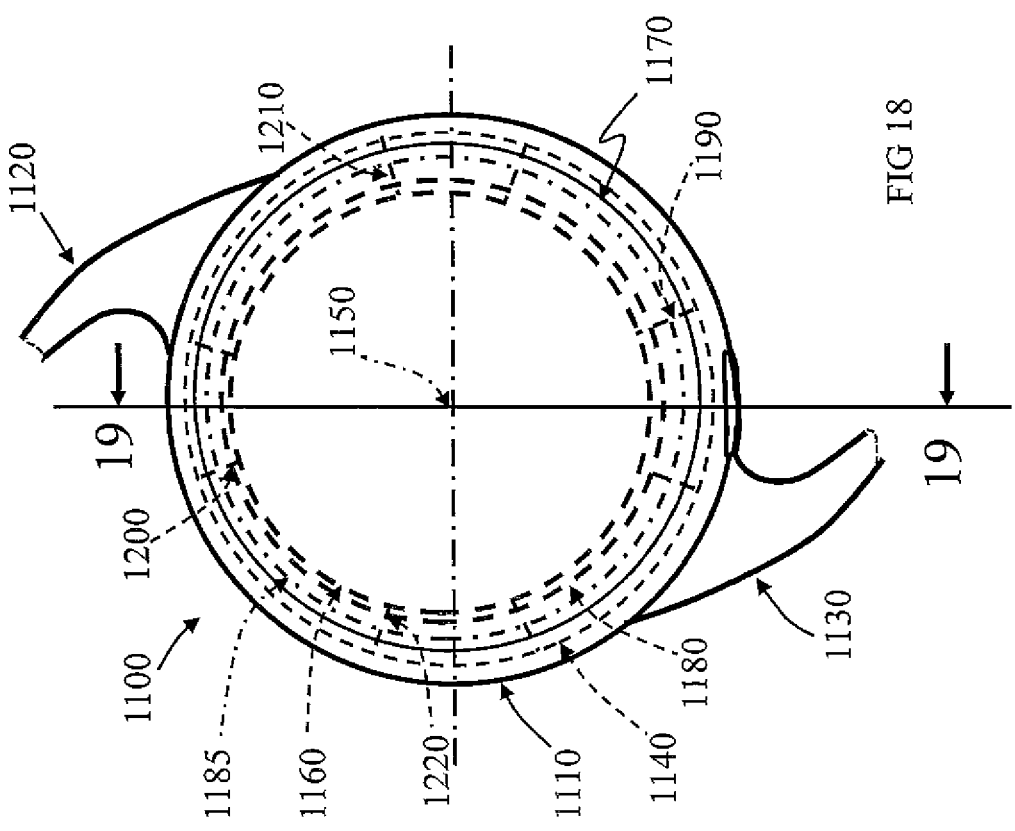

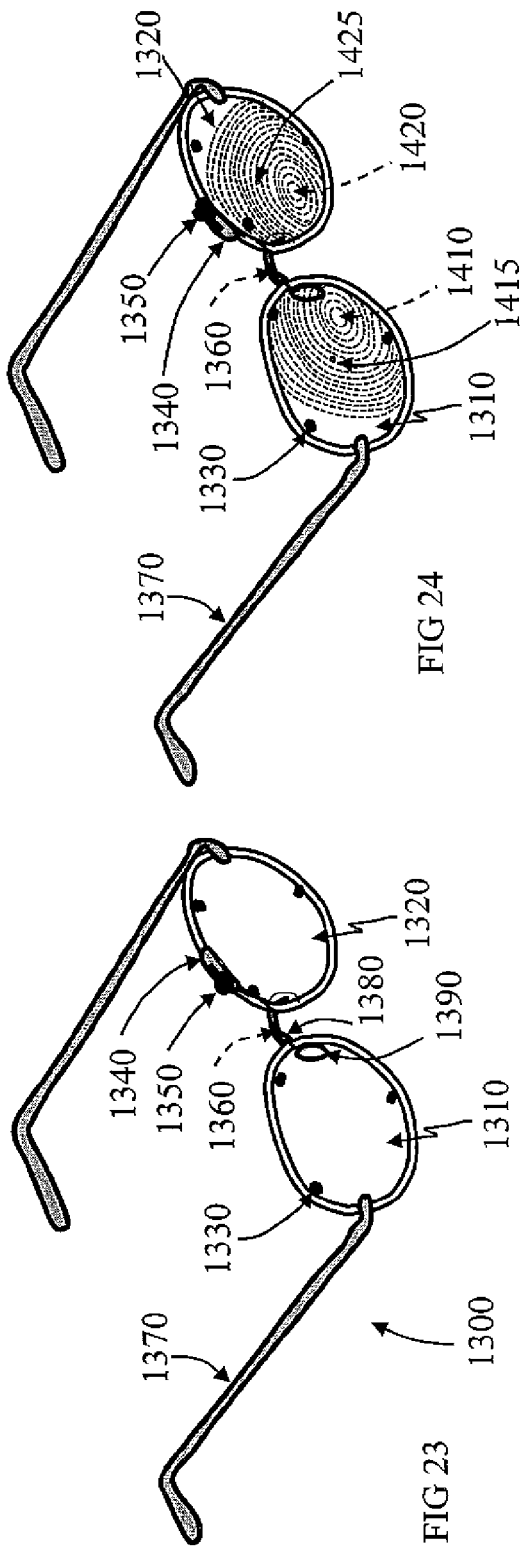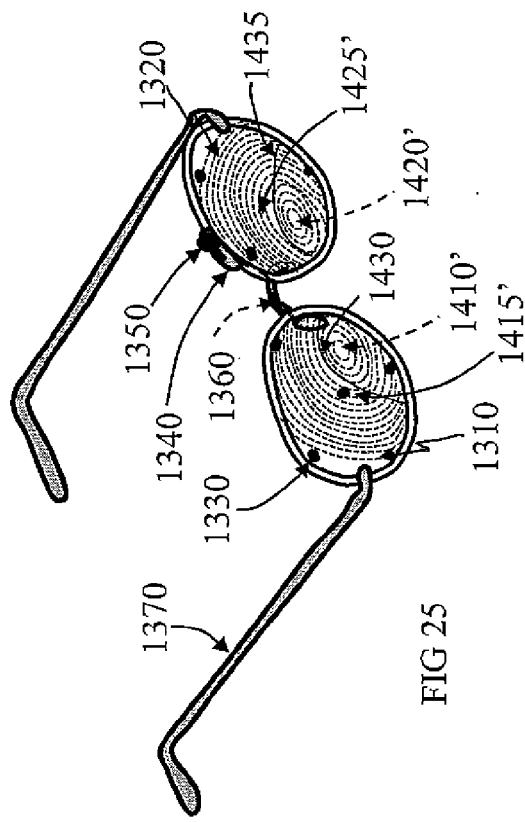
FIG 23
FIG 24
FIG 25

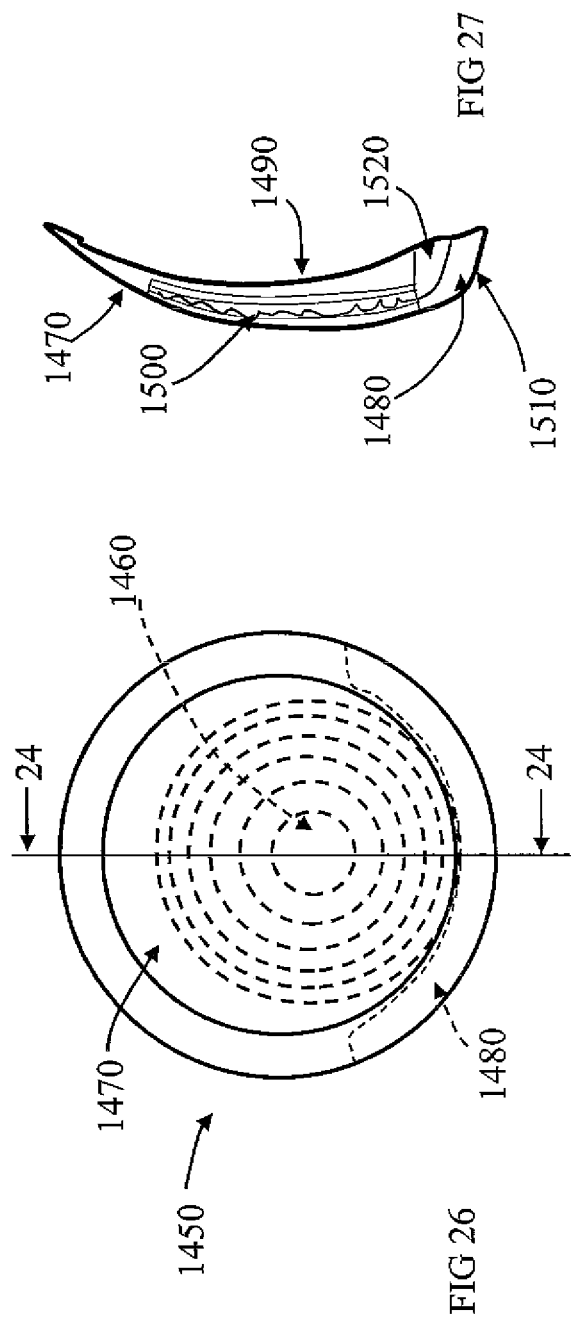

SWITCHABLE DIFFRACTIVE ACCOMMODATING LENS

This application claims priority from provisional application Ser. No. 61/514,413 filed Aug. 2, 2011 and is to be incorporated in its entirety.

FIELD OF THE INVENTION

The present invention relates generally to a diffractive lens that creates an image at different positions sequentially by the change in magnitude of the surface relief structure height at its diffractive surface, and more particularly to a diffractive ophthalmic lens that changes surface relief structure height at one of its surfaces to provide distance and near foci, and even more particularly to diffractive accommodating lens that changes surface relief structure height under the action of ciliary muscle.

BACKGROUND OF THE INVENTION

The diffractive lens of this disclosure can be applied outside or within ophthalmic application. In later case the lens is called ophthalmic lens. Ophthalmic lens in this disclosure is defined as a lens suitable for placement outside the eye such as spectacles or contact lenses or inside the eye such as aphakic and phakic intraocular lenses placed in posterior or anterior eye chamber and also included are less common vision correction lenses such as artificial corneas and corneal implants.

For detailed explanation of the lens of this invention, the application in the ophthalmology for Presbyopia correction and more particularly to accommodating optic is used as a preferred embodiment.

A fixed single power lens provides good quality vision but only within a small range of viewing distances that is usually significantly narrower than the range required from near to distant vision. The resulted vision deficiency is called Presbyopia. There is a significant effort to develop a lens for Presbyopia correction in a form of multifocal refractive or diffractive type lenses that provide multiple foci and also in a form of accommodating lenses that may change their external surface shapes or positions inside the eye for incremental power increase for near vision. Accommodating ophthalmic lens described in this disclosure is a lens that consequently changes the image positions between distance and near foci by directing most of the available light to different diffractive orders or between refractive state and one of the diffractive orders under the action of ciliary muscle. It is important to note that lens disclosed in this invention has application outside accommodation and outside ophthalmic.

Natural accommodation as vision phenomenon is the ability of the eye to focus at different distances. It involves the dioptric power change of the eye provided by the crystalline lens shape change. The accommodation is a multistage process and involves a number of ocular elements: ciliary muscle, ciliary body, zonules, and lens capsule and, at last, the crystalline lens itself, FIG. 1. It also involves dynamically opposite actions of the corresponding ocular elements such as ciliary muscle vs. zonules/capsular bag. For instance, to accommodate for near vision, the ciliary muscle contracts which moves the ciliary body inward towards the crystalline lens, this relaxes the zonules attached to the ciliary body which in turn, releases the elastic capsular bag to allow the crystalline lens inside the capsular bag to take a more rounded shape for higher optical power. For far vision, the ciliary muscle relaxes which moves the ciliary body outward from the crystalline lens; this creates tension on zonules which in turns stretches the capsular bag that flattens the crystalline lens inside the crystalline bag to reduce the optical power of the lens.

All the involved in accommodation ocular elements and especially zonules and capsular bag vary with age and between different individuals thus making an accommodating device that relies on the action of zonules and crystalline bag to work as an extremely challenging task.

It has been several efforts to develop ophthalmic lens that can switch between optical conditions for far and near vision since 80th by using refractive optic. The principle of adjustment can be divided into three types of approached: (1) deformable design that changes lens shape in order to change its power, (2) translatable design that changes lens position inside the eye in order to change eye power and (3) refractive index adjustment design that changes lens material refractive index in order to change its power. All these designs were disclosed for the applications to the ocular implants and spectacles; no application to contact lens has been uncovered.

There are numerous US patents on and descriptions of deformable designs (Fluid Vision, Flex Optic, NuLens, etc.) and translatable designs (Synchrony, Crystalens, HumanOptics, TetraFlex, etc.) for ocular implants where all of them utilize refractive optics. Deformable design was also applied to spectacles, for instance variable focus spectacle lens where the surface radius changes were described by Fujita and Idesawa (Fujita T and Idesawa M, "Accommodation Assisted Glasses for Presbyopia", Proceedings of the SPIE, 2002; 4902:99-109). The interesting aspect of this paper is the description of the gaze tracking for automatic lens power adjustment for viewing object distance.

There are also few US patents on refractive index modification designs. Nishimoto in U.S. Pat. No. 4,564,267 suggested a variable focal lens using the Pockels effect by applying electric filed to the electro-optic crystal to change material refractive index. Similar idea was disclosed by Kern in the U.S. Pat. No. 4,601,545 using liquid crystal. Kern also proposed the application of his invention to intra-ocular and spectacle lenses (Kern S P, "Bifocal, electrically switched intraocular and eyeglass molecular lenses" Proceedings of the SPIE, 1986; 601:155-158).

All the above disclosure was based on refractive optic for accommodation application. Diffractive lens application to accommodating implant was disclosed by Portney in US Patent Application No: 20070032866 where the monofocal diffractive optical surface changes its periods by bending in response to the accommodating force from the ocular element of the eye thus changing a separation between the diffractive orders and shifting the diffraction image focus from one position to another. Publication 20070032866 did not disclose a change in surface relief height to switch light from one diffractive order to another. This is to take full advantage of the diffractive optic to maintain constant Add power as the separation between the diffraction orders still relied on continuous change in focus position similar to a refractive optic.

Diffractive optic offers advantages over refractive optic for Presbyopia treatment where switching between far and near vision is required instead of continuous change of optical power of refractive optic where each power position is much more difficult to control and where far vision, for instance, may be easily varying even with a small change of accommodating force. More detailed explanation of diffractive optic advantages is provided below.

The advantage of the diffractive optic in switching between far and near over the refractive optic was described in the application to the spectacle lens by large group of researches:

Li G, Mathine D L, Valley P, et al. "Switchable electro-optic diffractive lens with high efficiency for ophthalmic application", Proceedings of the National Academy of Science of the USA, 2006; 103: 6100-6104. The operation of the described spectacle lenses was based on electrical control of the refractive index of thin layer of pneumatic liquid crystal. Though the approach is feasible, it is very complicated and expensive to execute and it also requires elective field control for its operation which is problematic for ocular implants and contact lenses. Haddock at el. in US Patent Application 20090256977 introduced further improvements to the above diffractive lens manufacturability. The spectacle lenses under the above design were released by PixelOptics under Em Power trade name.

The described above systems used the electro-optical switching between diffractive states for far and near vision by refractive index modulation. The present invention utilizes mechanical optical switching between far and near vision by changing the height of the surface relief structure of the diffractive optic.

The present disclosure also describes the diffractive optic with progressively changing foci by adjusting the periods of the diffractive grooves. This can be applied not only to the surface relief periodic structure of static single focus and multifocal diffractive lens where the light split is constant and also to dynamic diffractive lens where light is redirected between different diffractive orders by mechanical or electro-optical means of refractive index or surface relief modulations.

Iyer et al. in the US Patent Application 20110176103 referenced to refractive-diffractive insert that provided progressive power variation by optical communication between refractive and diffractive regions. No reference to a diffractive optic that on its own provides progressive foci by adjusting the periods of the diffractive grooves was disclosure in Iyer's US Application.

Diffraction principle of image formation is utilized for the disclosed accommodating ophthalmic lens. A diffractive lens consists of a periodic structure responsible for the separation between produced diffractive orders and is characterized by its phase function analogous to a refractive lens description by its surface sag equation. There two ways to change phase delay in the diffractive structure of a diffractive optical element and switch or redirect light between different foci, either by refractive index modulation or by surface shape (relief) modulation. Therefore, there are two types of diffractive structures: (1) refractive index modulation structure and (2) surface relief structure. First approach has been applied to spectacles as referenced above publication by Li and his colleagues. For the purpose of referencing in this disclosure, the first approach to switch or redirect light between different foci by refractive index modulation is called diffractive accommodating lens by refractive index modulation and the second approach to switch or redirect light between different foci by surface relief modulation is called diffractive accommodating by surface relief modulation.

The proposed invention is based on the modulation of the surface relief structure by maintaining its period and, therefore, separation between diffractive order and changing its height in order to control light distribution between the diffractive orders. In the other diffractive structure that relies on the refractive index modulation, the maximum thickness of the material within which the refractive index changes is analogous to the higher of the surface relief structure as explained above. For the purpose to simplify a description of the refractive modulation structure, the maximum thickness of the material within which the refractive index changes is defined as the "refractive index amplitude" in this embodiment.

The disclosed invention is applicable not only to spectacles lens but contact lenses and ocular implants. Thus, the surface relief structure of this invention maintains the same period but otherwise changes its height in order to provide accommodation between far and near vision.

A surface relief structure of diffractive surface can be formed by different types of zone or groove shapes (sine, rectangular, for instance) and a blaze shape shown on the FIG. 2 being the most common one. A specific periodic blaze shape is cut into a refractive surface which becomes the base surface of the diffractive surface and the resulted lens becomes a diffractive lens.

This disclosure will use blaze grating as an example but the present invention is applied to any type of surface relief diffractive surface that produces distance and near foci or, more generally, at least two images at its diffractive orders by shifting 100% or substantial portion (about 30% or more) of light to different diffraction orders or refractive image position and a position defined by one of the diffraction orders.

The distances from the diffractive surface to the foci created by the diffraction orders can be quantified in terms of diffraction powers associated with the diffraction orders similarly to a refractive lens power definition. Zero-order diffractive power of the diffractive surface coincides with the refractive power of the refractive surfaces formed by the base surface of the diffractive surface.

By the law of formation of a diffraction order, light can only be channeled along the diffraction orders of the diffractive lens where constructive interference can take place. It leads to the discrete foci of a diffractive lens. Discrete nature of image formation by a diffractive optic is the key characteristic utilized by the diffractive accommodating lens of this invention.

Importantly, the image is physically formed at a given foci of the diffraction order if a measurable percent of total light is actually channeled along a given diffraction order. This depends upon the light phase shift introduced by each blaze zone, i.e. groove height or blaze material thickness (h), FIG. 2. The construction of accommodating cell of the diffractive accommodating lens of this invention is to control the change of the blaze material thickness in order to channel 100% of light or most of the available light consequently between two diffractive orders or a diffractive order and refractive state where the grooves height is zero. These two image positions associate with far and near foci.

Geometry of the diffraction grooves is easier to explain by the "geometrical model" of the grating: 100% efficiency (light transmittance) in m-order can be achieved if the direction of the imaginable blaze ray defined by the refraction at the blaze coincides with the direction of m-order diffraction, (Carmifia Londofio and Peter P. Clack, Modeling diffraction efficiency effects when designing hybrid diffractive lens systems, Appl. Opt. 31, 2248-2252 (1992)). It simply means that the blaze material thickness is designed to direct the blaze ray along the m-order diffraction produced by the blaze groove widths for the design wavelength of light.

In a simple paraxial form the circular grating zones, also called grooves, echelettes or surface-relieve profile, can be expressed by the formula $r_j^2 = jm\lambda f$, i.e. the focal length of m-order diffraction ($m=\pm 1$, $\pm 2$, etc.) for the design wavelength ($\lambda$) can be closely approximated by the following formula:

$$f_m = \frac{r_j^2}{jm\lambda} \quad (1)$$

This is the formula typically used for the groove widths calculation in diffractive optic that produces wavefront close to a spherical shape, i.e. small amount of aberration. The locations of groove's borders are simply determined analytically by radii $r_j$. The radii per Equation 1 define diffractive lens periodic structure which, in this case, produces spherical wavefront that defines single focal length ($f_m$) for diffractive order (m). In general, the periodic structure can be surface relief structure where surface shape manifests the periodic structure per Equation 1 or close to it to produce quasi-spherical wavefront, or refractive index modulation structure where the material variation of the diffractive lens manifests refractive index periodic structure per Equation 1.

In case of the surface relief structure, and in the paraxial approximation the blaze material thickness to produce 100% efficiency at m-order is $$h_m = \frac{m\lambda}{(n-n')} \quad (2)$$

where n=refractive index of the lens material and where m=refractive index of the surrounding medium.

A surface relief may be formed by different shapes of the periodic diffractive structure and not only by a blaze shape and for the generality of the present invention the term "groove" is used as the description of the variety of shapes of the diffractive structure including multi-order phase grating (MOD) which is useful in reducing dispersion or chromatic aberration of the diffractive optical element.

Phase function defines diffractive optic analogous to sag equation defining refractive optic. A phase function is usually defines in polynomial form as shown by the equation 3 below, The examples of the phase functions in terms of polynomial phase coefficients is provided in the Table 3 for diffractive optic with small and large spherical aberrations.

In case of small aberration, the periodic structure of the diffractive optic is quite accurately defined by the equation 1 for given focal distance. In case of significant spherical aberration of the diffractive lens to be introduced in order to extend the range of vision around one of the focus of the diffractive order, the calculation of the groove shapes can be conducted numerically similar to the method described by Portney in the US Patent Appl. No: 20100066973 for multifocal diffractive lens:

a) calculating diffractive structure phase coefficients that produce diffractive focus of a selected accommodating state. Usually (−1)-order diffraction is allocated to near focus.

$$\Phi_{-1}(r) = \frac{2\pi}{\lambda}[a_1 r + a_2 r^2 + \ldots + a_n r^n] \quad (3)$$

Formula (3) is (−1)-order (near focus) phase function with phase coefficients $a_i$ calculated over the contribution of the eye optical system.

b) numerically calculating a 100% diffraction efficiency groove shape and height $h(r_i)$ that produces the defined phase coefficients and the groove widths defining by the phase function modulo $2\pi p$ cycle where p=1, 2, . . . .

The objective of the present invention is to provide a diffractive accommodating lens that offers a sequential change in the optical states with substantial portion of the available light switched or redirected between two images for far or near vision under the action of the ciliary muscle contraction and relaxation. The lens that forms images at two image positions with image at one image position is formed by non-zero order diffraction and image at another image position is fainted by either a different order diffraction or refraction is disclosed by this invention.

The invention offers also an option to bypass the ocular elements such as zonules and capsular bag which reduce a reliability of an accommodating lens and rely on the direct interaction with the ciliary muscle. This is accomplished due to the ability to the diffractive accommodating lens of this invention to switch foci between far and near vision by only a small amount of the material transfer which can be accomplished by the ciliary muscle action. A volume of the material transfer involved in the diffractive accommodating lens of this invention is only in a small fraction of milliliter.

A material transfer in accommodating optic may occur directly from a sensor cell implanted or installed next to ciliary muscle in order to respond to their relaxation and contraction. This is accomplished in ocular implants such as aphakic, phakic including corneal implants. A material transfer may occur indirectly from a sensor cell by the cell transferring electronic signal to an external visual aid such spectacles, for instance, to control its optical states between far and vision. Ultimately, electronic transfer signal can be conducted between sensor cell and implants with optical state change per these inventions by mechanical or electronic means.

As a minimum, the lens of the present invention may still rely on the interaction with the capsular bag or vitreous as indirect means to respond to ciliary muscle actions during accommodation.

The invention discloses different option for optical enhancement of the range of vision at image formed at the diffraction order on the example of extending the range towards intermediate vision from the near vision formed by (−1)-order diffraction.

In the present invention the periodic structure of the diffractive surface is maintained between the optical states of far and near vision but the phase delay changes between when switching between these optical states. The invention disclosure describes surface relief diffractive lens that switches optical states of far and near vision by changing phase delay with surface relief height.

Certain invention disclosures related to multi-zonal use of the diffractive surface the zones have different periodic structure to provide different foci for the same diffractive order is applicable to general phase delay wither by the height of the surface relief or refractive index modulation.

Additional invention disclosure describes periodic structure change to increase spherical aberration and associated with it depth of focus around focus position produced by non-zero diffractive order as compared with diffractive lens with small amount of spherical aberration. This disclosure is applicable to static diffractive multifocal lens where light split is constant as well as to dynamic diffractive accommodating lens where light split between far and near vision changes.

The invented lens can be applied outside the eye in a form of spectacles, contact lens or even in non-ophthalmic applications required the image position change without moving the lens itself.

SUMMARY OF THE INVENTION

A lens in accordance with the present invention consists of front and back surfaces and accommodating cell situated between them. In a particular embodiment, the accommodating cell consists of two chambers with at least one chamber filled with optical fluid with the refractive index matching the refractive index of the accommodating element separating the chambers. The accommodating element is having the surface relief structure that maintains its period but changes its height due the pressure difference between the chambers. The accommodating cell may include another chamber connected with the external to the lens medium (aqueous humour, air, stroma, tear layer). The accommodating cell may also have chambers both filled with optical fluids of different refractive indices. The accommodating element shape change creates different diffractive groove heights to redirect most of light that passes through the lens image forming zone between different image positions of far vision and near vision foci. The add power for near vision is defined by the periodicity of the surface relief structure. Thus, the accommodating element includes formable surface with a plurality of sub-elements disposed on it for temporarily establishing a surface zone with a non-zero relief structure height upon change of pressure on this formable surface. For instance, one focus can be refractive formed by the refractive surface with surface relief surface with zero heights and another focus is formed by the diffractive surface relief of specific non-zero height to direct most the available light that passes through the lens image forming zone along the corresponding to this height non-zero order diffraction. Another option is to have the one surface relief non-zero height to pass most of light along the corresponding to this height non-zero order diffraction and then to change the s height magnitude to direct most of the available light passing through the lens image forming zone to another corresponding to this height non-zero order diffraction.

This invention describes the device called diffractive accommodating lens or DAL which can overcome the complexity and individual dependence of the forces involved in eye accommodation. The disclosure involves two aspects of the invention:

(1) The diffractive accommodating system that includes Sensor Cell and DAL interacts directly with the ciliary muscle in changing its focus state. It is well known that the ciliary muscle operation is maintained for different age thus proving a reliable action for the accommodating device. All other ocular elements involved in the accommodation such as zolules, capsular bag and the crystalline lens itself are highly age and individual condition dependent and can't be relied on for consistent operation of accommodating devices. The invention discloses Sensor Cell that is placed at the location of the Scleral Spur to interact directly with ciliary muscle and transfer the pressure change to the Diffractive Accommodating Lens to change its states between far and near vision. A diffractive accommodating lens DAL according to this invention may also rely on the secondary accommodating effect where ciliary muscle contraction effects the choroid tension that increases vitreous pressure that causes crystalline lens-zonule complex to move forward. In this case, the crystalline lens is replaced by the DAL and the vitreous pressure change switches the states of the DAL between far and near vision.

(2) The diffractive accommodating lens DAL provides two states of accommodation for far and near vision thus maintaining each state only temporary. Technically it means that the device acts in digital binary sense and does not change its accommodation effect if a force exerted by ciliary muscle does not exceed certain threshold level. This allows maintaining stability of the vision in relaxed state even under some fluctuation of the forces. Thus, the operation of DAL relies only on a single parameter such as a force threshold between relaxed and contracted states of the ciliary muscle of a given individual which can be even adjusted in vivo.

A diffractive lens that directs 100% or most of the available light that passes through its image forming zone to (−1)-order diffraction is called kinoform and the corresponding diffractive lens acts as one of the states of the diffractive accommodating lens DAL of this disclosure, specifically for near focus. A diffractive lens that directs 100% of most of the available light to (+1)-order diffraction may also act as one of the states of the diffractive accommodating lens DAL of this disclosure, specifically for far focus.

Multifocal diffractive lens is also used to provide two image positions for far and near vision for Presbyopia treatment but the issue with this type of design is that in-focus image at each image position includes out-of-focus image resulted in blur that reduces each image contrast and contributing to halo and glare perception. One way to quantify multifocal diffractive lens imaging is to state that total amount of light used to form in-focus images at certain aperture size is less than total amount of the available light entering the lens within the same aperture size. The reason is that the light is split between in-focus images at two image positions to form both in-focus images simultaneously.

In case of diffractive accommodating lens of this invention, light utilizes much more efficiently, the total amount of light used to form in-focus images at certain aperture size exceeds the total amount of light entering the lens within the same aperture size. The reason is that both in-focus images form sequentially by redirecting some light from in-focus image at one image position to in-focus image at another image position. It is possible that the diffractive accommodating lens of this also invention also split light between the images at two image positions simultaneously but the use of light for in-focus image is higher than in multifocal diffractive lens because the some or all amount of light is redirected inform in-focus image at one image position to the in-focus image in another image position. This improves image contrast and reduces halo and glare as compared with multifocal diffractive optic.

The preferred embodiment creates the change between the optical states of the acting surface by changing pressure between the chambers located at both sides from the surface but, in general, the surface shape change from one diffractive order to another or to refractive state for directing most of the light to one or another image positions can be accomplished by other means including mechanical transducers or electrical or magnetic force.

The present disclosure also describes the diffractive optic with progressively changing foci by adjusting the periods of the diffractive grooves. This can be applied not only to the surface relief periodic structure of static single focus and multifocal diffractive lens where the light split is constant and also to dynamic diffractive lens where with light is redirected between different diffractive orders by electro-optical or mechanical means by refractive index or surface relief modulations. The mechanical means of surface relief modulation to provide dynamic switch between far and near vision is provided in this invention disclosure.

BRIEF DESCRIPTION OF THE DRAWINGS

The advantages and features of the present invention will be better understood by the following description when considered in conjunction with the accompanying drawings, in which:

FIG. 1 illustrates a portion of eye anatomy related to the accommodation process. The ciliary body of the eye has three basic functions: aqueous production and removal, accommodation, and the formation of vitreous mucopolysaccharide. The ciliary muscle initiates the accommodation process and situates inside the ciliary body.

FIG. 2 illustrates a prior art diffractive lens with blazed periodic structure forming different diffraction orders along which the light can only be channeled. It illustrates the optical principle used by the accommodating cell of this invention for switching between far and near vision. The FIG. 2 also illustrates a "geometrical model" of the diffractive lens through the relationship between the imaginary blaze ray defined by the refraction at the blaze and directions of the diffraction orders.

FIG. 3 shows a simplest form of the accommodating cell configuration as a rectangular disc of about 4-6 mm diameter and about 0.1-0.3 mm thickness. The minimum diameter of the accommodating is around 3 mm and may reach about 6 mm diameter. The thickness can be as small as about 0.1 mm. The accommodating cell is situated inside the lens or it may take the shape of the lens itself by including required surface curvatures by its external surfaces instead of flat surfaces shown in the FIG. 3.

FIG. 4 demonstrates a cross-section of a preferred embodiment of an accommodating cell in a relaxed state. The accommodating cell of this embodiment includes two chambers filled with optical fluids, silicone fluid, for instance, separated by the membrane called accommodating element that has the ability to change its surface shape with a difference in pressure between the chambers. One chamber is filled with optical fluid of matching refractive index as the material of the accommodating element separating the chambers to make the light passing between the material separating the chambers and the optical fluid undisturbed by the surface shape facing this chamber. This is optically transparent chamber or OTC. Optical fluid of non-matching refractive index fills the other chamber. Thus, a light refraction takes place only at the surface facing this chamber. This is optically active chamber or OAC. The FIG. 4 demonstrates that the surface facing the chamber filled by optical fluid of non-matching refractive index (OAC) is smooth refractive surface type for Far vision in relaxed state as one of the examples of surface configuration.

FIG. 5 demonstrates a cross-section of the accommodating cell, shown in FIG. 4, in a stressed state. The accommodating element between the chambers takes a shape of diffractive surface manifested by the diffractive grooves facing the chamber filled with optical fluid of non-matching with the accommodating element material refractive index (OAC). The maximum diffractive grooves heights (blaze material thickness) is restricted by the geometry of the accommodating element and the thickness of the chamber filled with optical fluid of matching refractive index (OTC), i.e. most of the available light passing the image forming optical zone of the diffractive accommodating lens is directed to (−1)-order diffraction by the created diffractive surface of the accommodating element.

FIG. 6 demonstrates a cross-section of a preferred embodiment of an accommodating cell in a relaxed state. The accommodating cell of this embodiment includes two chambers the first one is filled with optical fluids, silicone fluid, for instance, and the second chamber is connected with the external medium surrounding the ophthalmic lens (aqueous humour in case of intraocular lens, stroma or air in case of corneal implant, tear layer or air in case of contact lens and air in case of spectacle lens). The chambers are separated by the membrane called accommodating element that has the ability to change its surface shape with a difference in pressure between the chambers. First chamber is filled with optical fluid of matching refractive index as the material of the accommodating element separating the chambers to make the light passing between the material separating the chambers and the optical fluid undisturbed by the surface shape facing this chamber. This is optically transparent chamber or OTC. Thus, a light refraction takes place only at the surface facing the chamber. The second chamber is optically active chamber or OAC. The FIG. 6 demonstrates that the surface facing the second chamber is smooth refractive surface type for Far vision in relaxed state as one of the examples of surface configuration.

FIG. 7 demonstrates a cross-section of the accommodating cell, shown in FIG. 6, in a stressed state. The accommodating element between the chambers takes a shape of diffractive surface manifested by the diffractive grooves facing the second chamber connected to the external medium of the ophthalmic lens. The maximum diffractive grooves heights (blaze material thickness) is restricted by the geometry of the accommodating element and the thickness of the second connected with external medium, i.e. most of the available light passing the image forming optical zone of the diffractive accommodating lens is directed to (−1)-order diffraction by the created diffractive surface of the accommodating element.

FIG. 9 illustrate front view of one of the embodiments of intraocular lens consisting of lens optic, haptics or supporting elements and addition of the connecting flexible element attached to the accommodating element situated inside the intraocular lens of this embodiment. The connecting element is to connect the accommodating element with the sensor cell that interacts with the ciliary muscle to transfer the force from the ciliary muscle contraction and relaxation into a difference in pressure between the chambers of the accommodating cell.

FIG. 10 shows the cross-section of the intraocular lens of FIG. 7. It demonstrates the accommodating cell situated inside the intraocular lens with connecting element attached to it at one end and the other end attached to the opposite edge of the intraocular lens optic for its temporary fixation during the lens implantation inside the eye. This end of the connecting element is separated from the intraocular lens after the implantation connection to the sensor cell.

FIG. 11 illustrates the assembly of the intraocular lens shown on the FIGS. 7 and 8. The intraocular lens assembly of this particular embodiment consists of three elements: front element which can be attached to the back element by the front wedge and the accommodating cell placed between them. Simplest plano-convex shape of the front element allows making inexpensive variation of its optical characteristics such as dioptric power, asphericity and toricity for astigmatism correction. Back element of this example incorporates also haptics and is of more complex shape and is less variable element of the intraocular lens. Accommodating cell is secured inside the lens to allow the overall intraocular lens to demonstrate a conventional shape of a typical non-accommodating lens.

The shape of the sensor cell of this embodiment consists of two plates with each chamber situated inside each plate. Each plate has hard exterior shell and soft interior membrane to respond to the force from the ciliary muscle and transfer a small amount of material between corresponding chambers of the sensor cell and accommodating cell to change the shape of the accommodating element separating the chambers in the accommodating cell. Only small amount of material transfer, small fraction of milliliter, is required to form diffractive surface for near vision from refractive surface for far vision as shown in this example of the invention.

Figures 12, 13:
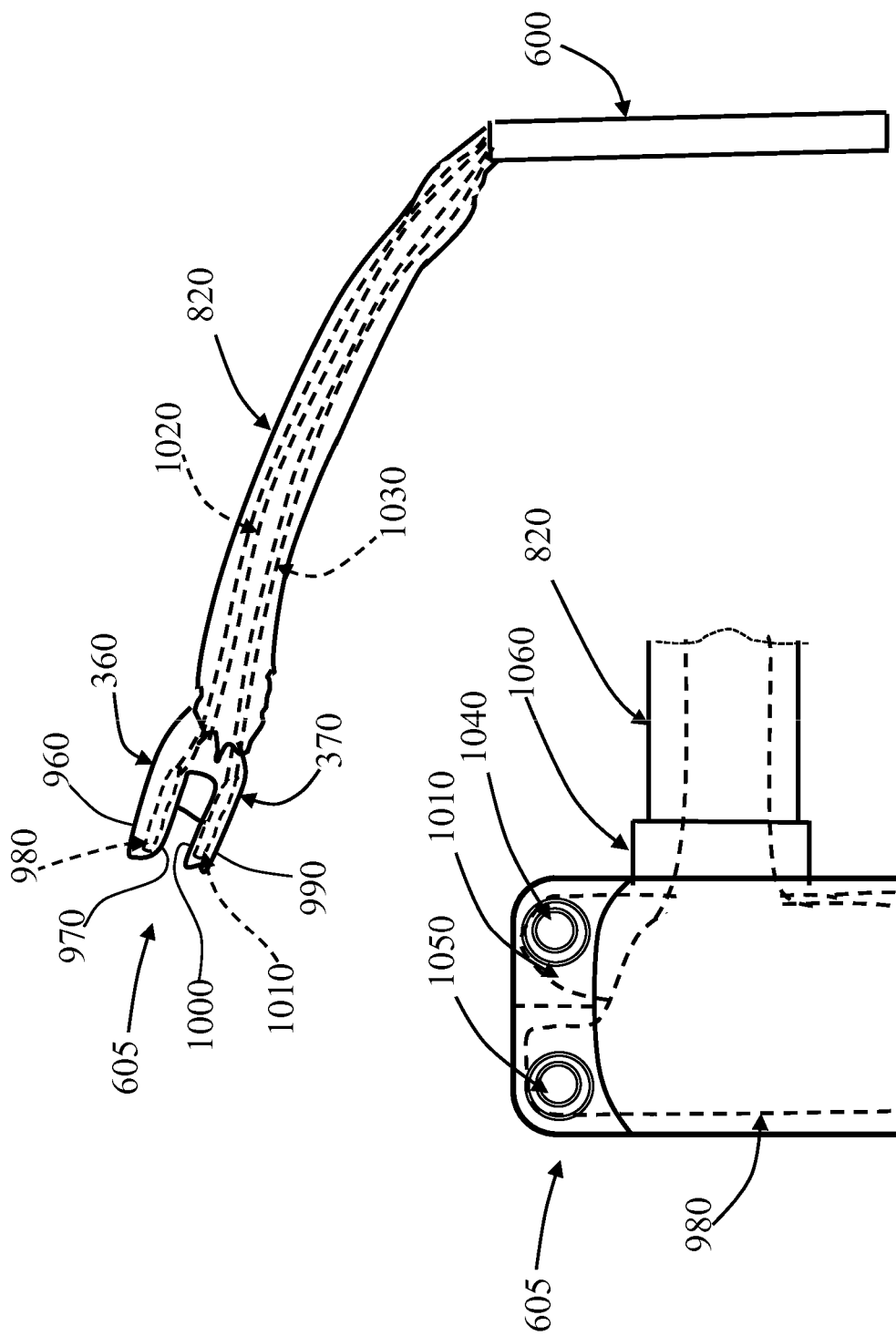
FIG. 12 illustrates the connection between sensor cell and accommodating cell. The connecting element is about 6 mm in length which is adequate to place the sensor cell at the proximity of the ciliary muscle or more specifically, at the scleral spur for the interaction. The sensor cell consists of two elements with chambers connected with the corresponding chambers of the accommodating cell. These elements of the sensor cell are placed externally and internally to the ciliary muscle fibers (scleral spur) to create differential pressure between the chambers of the sensor cell with muscle contraction or relaxation—pressure at the internal to the muscle chamber increases and external to the muscle chamber reduces with the muscle contraction and returns to the original condition with muscle relaxation.

FIG. 13 shows the exterior view of the sensor cell in order to illustrate some specifics of the sensor cell in this example. It includes two ports each connecting with each chamber of the sensor cell to allow pressure adjustment between the chambers after in-vivo installation into the patient and connection with Diffractive Accommodating Lens. This is in order to adjust for a proper pressure threshold between the chambers to reliably switch between the optical states for far and near vision with the ciliary muscle contraction and relaxation which may depends upon the patient physiology and sensor cell installation.

FIG. 14 demonstrates aphakic Diffractive Accommodating Lens of this invention which replaced the natural crystalline lens. The FIG. 12 demonstrates the placement of sensor cell at the location of anterior tendon that includes scleral spur. Alternatively, it can be installed at the posterior tendon at the area of ora serrata. The sensor cell is placed with the exterior chamber being exterior to the ciliary muscle and the interior chamber to the interior to the ciliary muscle. The FIG. 12 demonstrates two paths for connecting element: through the ciliary sulcus posterior to the iris or iridocorneal angle anterior to the iris. Later will involve an iridotomy by making a puncture-like opening through the iris without the removal of iris tissue for the connecting element. The advantage of iridocorneal angle path is that it is more similar to the already developed glaucoma surgery technique that involves glaucoma shunt installation.

FIG. 15 demonstrates Diffractive Accommodating Lens (DAL) of this invention which compliments a previously installed aphakic convention IOL which is lacking Presbyopia correction. The DAL is placed in the commonly acceptable position at the ciliary sulcus in front of the previously implanted conventional IOL. The sensor cell and its connection with the DAC is similar to one described in the FIG. 12.

FIG. 16 demonstrates phakic Diffractive Accommodating Lens (DAL) of this invention that does not involve a removal of the natural crystalline lens. The DAL is placed in the iridocorneal angle or by the iris fixation. The sensor cell and its connection through the iridocorneal angle with the DAC is similar as one described in the FIG. 12.

FIG. 17 demonstrates corneal implant Diffractive Accommodating Lens (DAL) of this invention. The DAL of appropriate shape and thickness is placed in the cornea and connected to the sensor cell installed as described in the FIG. 12. The procedure does not require a penetration inside the eye.

FIG. 18 demonstrates a front view of aphakic Diffractive Accommodating Lens (DAL) of this invention which replaced the natural crystalline lens and relies on vitreous pressure or capsular bag tension change for switching between far and near vision. These environmental changes caused by ciliary muscle action affect the DAL directly without a need of sensor cell.

FIG. 19 demonstrates cross-section of the aphakic Diffractive Accommodating Lens (DAL) of FIG. 16 which replaced the natural crystalline lens but relies on vitreous pressure or capsular bag tension change for switching between far and near vision.

Figure 20:
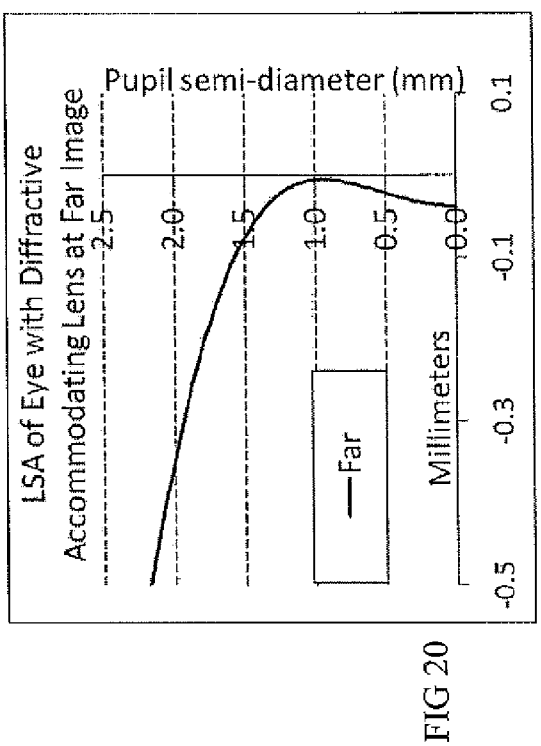
Figure 22:
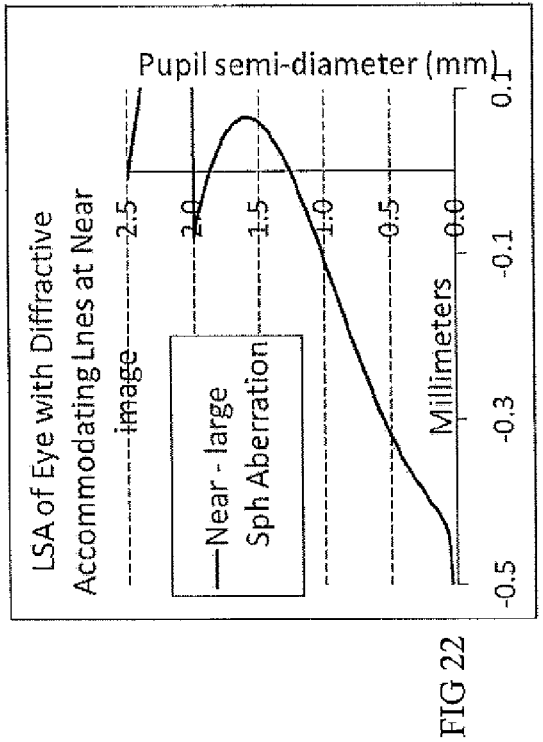
Figure 21:
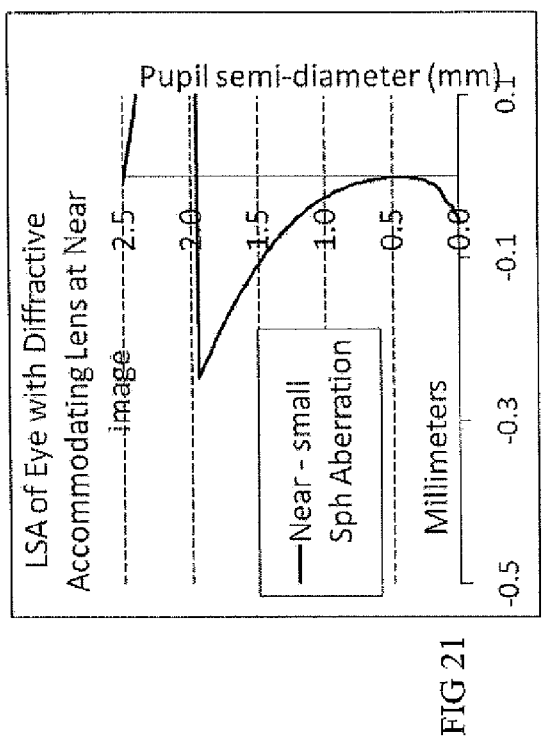

FIG. 20, FIG. 21 and FIG. 22 demonstrate optical characteristics of Diffractive Accommodating Lens of particular optical design in the eye in terms of longitudinal spherical aberration graphs (LSAs) at Far image and Near images. Two optical designs for near vision are shown as the examples.

FIG. 23 and FIG. 24 illustrate diffractive accommodating spectacles. The DAL spectacles allow to maintain large range of field for both distance and near vision and also to achieve automatic accommodation between far and near vision.

FIG. 25 illustrates diffractive accommodating spectacles with the accommodating cell divided into two zones, one to produce near focus in stressed condition and another to produce intermediate focus in stressed condition.

FIG. 26 and FIG. 27 demonstrate Diffractive Accommodating Lens application to contact lenses. The diffractive accommodating contact lens can provide accommodation between far and near vision without a need for the lens precise movement on the eye required for alternating or segmented contact lens or without compromising image contrast and overall image quality as in simultaneous vision multifocal contact lenses.

DETAILED DESCRIPTION

FIG. 1 illustrates a portion of eye anatomy related to the accommodation process. The ciliary body 100 has three basic functions: aqueous production and removal, accommodation, and the formation of vitreous mucopolysaccharide. The ciliary muscle initiates accommodating process and situates inside the ciliary body 100. The ciliary muscle contains three types of fibers: longitudinal 110, radial 120 and circular 130 fibers.

The accommodation function is the primary objective of this invention and the first order is to describe the ciliary muscle including their anatomy.

The ciliary body 100 is somewhat triangular in meridional sections and present circumferentially around the internal surface of the eye globe. It is narrower nasally (4.5-5.2 mm) than temporally (5.6-6.3 mm). The anterior margin of the ciliary body 100 is at the scleral spur 150 is about 1.5 mm posterior to the corneal limbus 160 in the horizontal meridian and 2 mm posterior in the vertical meridian. Corneal limbas 160 separates sclera 200 and cornea 240. Ciliary body 100 terminates posteriorly at the ora serrata 170 where the eye retina starts and which is approximately 7.5 to 8 min posterior to the corneal limbus 160 temporally, 6.5 to 7 mm nasally, and 7 mm inferiorly and superiorly.

Interiorly and externally, the ciliary body 100 forms a part of the posterior portion of the anterior chamber angle. The iris 180 is attached to its anterior and internal surface. Internally, it lies free and extends internally slightly anterior to the equator of the crystalline lens 190. Externally, it is adjacent to the sclera 200 with the perichoroidal space between the two. The internal surface of the ciliary body 100 is adjacent to the vitreous 210. The space formed by the posterior surface of the iris 180 and the internal and slightly anterior projection of the anterior-most ciliary processes 140 is called the ciliary sulcus 220.

The greater part of ciliary muscle is composed of external longitudinal fibers 110 running anterior-posterior on the inner aspect of the sclera 200 to insertion into the where muscle stars are produced referred to as episcleral stars close to ora serrata 170. This muscle is attached to the back of the eye via an elastic membrane at the suprachoroid (about 8 mm behind the Embus 160) in the region of the ora serrata 170. Its contraction pulls the ciliary body 100 forwards and inwards by 0.5 mm during maximum accommodation. As a result, periphery of the vitreous 210 is also compressed so that the lens 190 moves forward. The mechanism of vitreous compression is used in some accommodating IOL design by Cumming, U.S. Pat. No. 5,476,514 and others and is referenced in this disclosure as secondary accommodating effect.

The middle radial 120 and internal circular 130 fibers form a meshwork. The middle radial fibers 220 run obliquely to merge and attach to the ciliary processes 140. The innermost edge of the ciliarly muscle contains primarily circular fibers 130. It appears that circular fibers 130 run in a circle around the ciliary body 100 concentrically with the root of iris 180. Their sphincter like action contracts the ciliary ring around the lens 190 and thereby relaxing the anterior and posterior zonules 230. The anterior portion of the radial and circular fibers project anteriorly and centrally along a line approximately 45 degrees to the sclera plane. The ciliary body moves internally by about 0.34 mm and the equator of the capsule moves internally by about 0.25 mm with the muscle contraction.

The architecture of all three types of fibers has some general principles. All 3 are attached anteriorly at the ciliary tendon (scleral spur 150 and surrounding soft tissue) as Y shaped extensions with the Y inserting anteriorly into the tendon. The radial fibers 120 connect to relatively distant parts of the ciliary tendon and additional anterior fiber attachment to the iris 180. The tension on Scleral Spur effects corneal power so very slightly, less than 0.1 D and called in this disclosure as 3rd order accommodating effect. The uniqueness of this invention is to install a Sensor Cell described below at the area of ciliary tendon which has easy access. The sensor cell of this invention is used to transfer the effects of ciliary muscle contraction and relaxation in a form of pressure change to the accommodating cell of this invention situated inside the diffractive accommodating lens DAL in order to switch its states between far and near vision.

The maximum force of contraction of the entire muscle (radial force extended from ciliary muscle onto the lens 190) increases from $0.85 \times 10^{-2}$ N at age 15 to about from $1.3 \times 10^{-2}$ N at age 45 and then drops to about from $1.1 \times 10^{-2}$ N at age 55. The entire contraction force reaches the maximum (for accommodation of about 2.5 D) of $1.2 \times 10^{-2}$ N ($\approx 1.2$ g) at age 43 and, importantly, the ciliary muscle action is maintained throughout the age thus maintaining the effectiveness of the Sensor Cell.

The aqueous production by ciliary processes 140 together with the flow of aqueous 250 to the trabecular meshwork 260 and Schleman's canal 270 are essential for maintaining normal internal eye pressure and significant body of technology has been developed to treat the aqueous flow abnormality that lead to glaucoma. Different surgical techniques and devices (glaucoma shuts, for instance) have been developed for placement in the area of Schleman's canal 270. It has appeared that the application of the devices for glaucoma is practically at the intended placement of the sensor cell at the scleral spur 150 which is posterior of Schleman's canal 270 by only 1 mm and surgical techniques developed for glaucoma can be applied to the accommodating system (sensor cell and DAL) of this invention.

FIG. 2 describes a portion of a prior art ophthalmic device with diffractive surface 300 with blazed periodic structure 350. It also explains the optical principle used by accommodating cell of this invention for switching between far and near vision.

The FIG. 2 includes input light ray 320 refracted at the diffraction surface blaze and creating diffraction orders indicated by the directions 320a, 320b, 320c, etc. along which the exited light can only be channeled. In this case, direction of (+1)-order diffraction is shown by 320a and (−1)-order diffraction by 320c but there are infinite orders of diffraction.

FIG. 2 incorporates an explanation of the "geometrical model" of diffractive lens by including blaze ray 330 as the ray corresponding to the refraction of the input ray 320 as being theoretically refracted at the blaze. It is imaginable ray in the geometrical model of diffractive optic and coinciding with a real ray in terms of creating the actual image in the direction of the ray only if the blaze ray coincides with the direction to a diffraction order. The direction of the blaze ray 330 in the FIG. 2 differs from the direction of 0-order diffraction 320b due to the different refraction angles of the rays at the base curve 340 and surface relief or blaze structure 350. A particular blaze angle is created by the selection of the groove height or blaze material thickness (h).

If the blaze material thickness (h) is zero than the blaze structure 350 coincides with the base curve 340 and the lens becomes refractive type. If the blaze material thickness (h) increases to refract the blaze ray 330 along, say, (−1)-order of diffraction 320b as shown in the FIG. 2, the lens becomes a Kinoform with 100% efficiency at (−1)-order diffraction, i.e. theoretically, 100% of light passing through the lens is directed to (−1)-order diffraction. In the prefer embodiment of the diffractive accommodating lens design the state with zero blaze material thickness is selected to create the optical power for Far vision (Far power) and non-zero blaze material thickness is to direct most light along (−1)-order diffraction by the diffractive accommodating lens for optical power for Near vision (Near power).

The periodic structure, i.e. radii of the diffraction grooves, defines the separation between the diffraction orders. This periodic structure is shown as surface relief structure if blaze shape in the FIG. 2 where the geometrical model is applied to. The surface relief structure can take different shape of the diffraction grooves. The periodic structure may also be in the form of refractive index modulation structure where the thickness of the material layer of different refractive index modulates with certain period to produce diffraction orders.

FIG. 3 shows a simplest form of the Accommodating cell shape as a rectangular disc of about 4-6 mm diameter D and about 0.10 to 0.3 mm thickness W. The accommodation cell is made of transparent materials and acts as a lens with optical axis 590. The accommodating cell diameter acts as the image forming zone of the lens. In general, the accommodating cell may be curved to take a desirable shape.

The accommodating cell is situated inside the Diffractive Accommodating Lens or it may take a shape of the lens by including necessary curvatures by its external surfaces.

FIG. 4 demonstrates cross-section of the accommodating cell 600 with optical axis 590 in the relaxed state when ciliary muscle is relaxed. The accommodating cell 600 of this embodiment includes two chambers 640 and 650 filled with optical fluids (silicone fluids, for instance) separated by the wall called accommodating element 610 that has the ability to change its surface shape with a difference in pressure between the chambers 640 and 650. One chamber 640 filled with optical fluid of matching refractive index to the accommodating element 610 separating the chambers to make light passing between the accommodating element separating the chambers and the optical fluid of the chamber 640 undisturbed by the surface shape facing this chamber 640. Optical fluid of non-matching refractive index fills the other chamber 650. As a result, light refraction only takes place at the surface 560 facing the chamber 650. Chamber 640 is called optically transparent chamber (OTC) and chamber 650 is called optically active chamber (OAC). The FIG. 4 demonstrates that the surface 560 facing the chamber 650 with non-matching refractive index is smooth and continuous to form refractive surface type per this preferred embodiment.

Construction of the accommodating cell in general can be to change pressure in optically transparent chamber first to drive the change of the shape of the accommodating element to change the states between far and near vision or in optically active chamber first or simultaneously in both chambers as it is explained below with interaction with dual-chamber Sensor Cell, for instance.

Exterior of chamber 640 is limited by the membrane 620 and the chamber 650 is by the membrane 630. The accommodating element 610 consists of accommodating sub-elements 680, 690, 700, 710 and so on. The central sub-element is shown as solid piece situated in contact with membranes 620 and 630 at the center via corresponding pins 660 and 670 in order to assist with assembly of the accommodating cell and also to maintain the accommodating cell shape integrity for both membranes 620 and 630.

The central sub-element is fairly small; a fraction of millimeter in diameter and its shape facing the chamber 650 may be either flat or curved corresponding to the power for far, near or between far and near. In any case, it is too small to noticeably affect the overall image quality for eye far or near image. All other sub-elements are shown with flat surface 560 facing chamber 650. The sub-elements 690 and 700 are separated by substantially thinner material portion 570, which is repeated for all other sub-elements outside the central sub-element 680. These circular material portions are thin enough to provide bending of the sub-elements in case of certain level of difference in pressure between the chambers 640 and 650. Another side of the sub-elements indicated as 580 for sub-element 690 as the same as for others is also thinner than the rest of each sub-element thickness to assist with each sub-element bending.

The separation between the sub-elements and membrane 620 is of width H limiting the maximum bending of all sub-elements. The face 575 of the sub-element 690 facing the neighboring sub-element 700 is narrowed towards its edge between face 575 and face 585 to prevent bending the sub-element 690 towards chamber 650. The same construction is applied to all other sub-elements. Thus, bending of each sub-element is restricted towards the chamber 640 by the maximum dimension H which is somewhere in the range of 10-20 microns, depending upon the material refractive indices of the accommodating element and not matching optical fluid and targeted power difference between far and near vision. Below, the disclosure offers the specific example of the accommodating element construction.

All sub-elements have circular shapes around the optical axis 590. Though the chamber 640 is shown in the cross-section as being divided by the sub-elements into sub-chambers, all these sub-chambers are connected with each other by the radial channels.

FIG. 5 demonstrates a cross-section of the accommodating cell 600 with optical axis 590 in the stressed state when the ciliary muscle is contracted. As a pressure in the chamber 650 increases because of some optical fluid is squeezed into it by the accommodation action, the sub-elements 690, 700, 710 and so on bend at the thinnest places 720 and so on to create surface relief structure of the diffractive surface of the accommodating element 610. The maximum bending is limited to the magnitude H which is the width of the chamber 640 resulting in the equivalent groove height or blaze material thickness to produce the Kinoform, i.e. to direct most of the available light in the direction of (−1)-order diffraction for near vision.

The accommodating element 610 between the chambers 640 and 650 takes a shape of surface relief of, more specifically, shape of blazes to form diffractive grooves 740, 750, 760 and so on facing the chamber 650 filled with non-matching with the material of the accommodating element refractive index. The diffractive surface relief heights (blaze material thickness) is restricted by the geometry H of the accommodating element to create the Kinoform with the focus for near vision, i.e. 100% of light or most of the available light is directed to (−1)-order diffraction by the created diffractive surface relief surface of the accommodating element 600.

The accommodating element 610 takes shape of blaze of groove height H if the difference in pressure between the chambers 640 and 650 exceeds certain threshold ΔP. If the difference in pressure below this threshold ΔP then the light split between far and near foci similar to a multifocal diffractive lens. Nevertheless, the benefit of diffractive accommodating lens of this invention is that light split occurs only in stressed state for near vision where halo and glare is usually not the issue because of the presence of significant ambient light required for near vision, The refractive surface of the accommodating element 610 of FIG. 4 does not manifest diffractive grooves but, for generality, the refractive surface is defined as the extreme condition of the surface relief structure of the diffractive surface of the accommodating element 610 of FIG. 5 with surface relief structure height equals zero. Thus, one can say that the refractive surface of the accommodating element 610 of FIG. 4 has the same periodic structure as the diffractive surface of the accommodating element 610 of FIG. 5 but their height is zero. In general terms, the diffractive surface of the accommodating element 610 is called surface-relief structure which is not limited to a particular groove shape and the refractive surface 560 of the FIG. 4 is considered as the special case of the surface-relief structure of the same period but zero height.

Theoretically, the created Kinoform directs 100% of light to near focus. Due to the construction restriction, the diffraction efficiency at (−1)-order is reduced by the surface shape of the bent material portion 720 and alike between all sub-elements:

$$\eta_{-1} \approx \left(\frac{\Delta r'}{\Delta r}\right) \quad (1)$$

where Δr' is reduced from the theoretical period Δr of groove equaled to the width of the sub-element due to so called "shadowing", in this case light passing through 720 and alike is out of phase for constructive interference at near image from all sub-elements. The average groove width Δr is in the order of 0.1 mm and the width of thin material portion 720 is about 10th of it dimension leading to a theoretical diffractive efficiency for near vision of about 90%.

The surface relief structure of the Accommodating element 610 is constructed to produce the same single focus by all its sub-elements in stressed condition of ocular implants and spectacle lens in order to maximize the image quality. In case of a spectacle lens application where eye rotates and viewing through different portions of the spectacle lens, there is a benefit to divide the accommodating element into zones with different periods of surface relief structures of the zones. Under a stressed condition, the surface relief structure in each zone direct light to different foci of each zone (−1)-order diffraction. Thus, one zone may be for near focus and another zone is for intermediate focus and both foci come into play simultaneously under stressed condition.

FIG. 6 demonstrates cross-section of the accommodating cell 600' with optical axis 590' in the relaxed state when ciliary muscle is relaxed. The accommodating cell 600' of this embodiment includes two chambers 640' and 650' where first chamber 640' is filled with optical fluid (silicone fluids, for instance) and other chamber 650' is connected to the external medium of the ophthalmic lens. They are separated by the accommodating element 610' that has the ability to change its surface shape with a difference in pressure between the chambers 640' and 650'. The chamber 640' filled with optical fluid of matching refractive index to the accommodating element 610' separating the chambers to make light passing between the accommodating element separating the chambers and the optical fluid of the chamber 640' undisturbed by the surface shape facing this chamber 640'. As a result, light refraction only takes place at the surface 560' facing the chamber 650'. Chamber 640' is optically transparent chamber (OTC) and chamber 650' is optically active chamber (OAC). The FIG. 6 demonstrates that the surface 560' facing the chamber 650' is smooth and continuous to form refractive surface type per this preferred embodiment.

Exterior of chamber 640' is limited by the membrane 620' and the chamber 650' is by the membrane 630'. The accommodating element 610' consists of accommodating sub-elements 680', 690', 700', 710' and so on. The central sub-element is shown as solid piece situated in contact with membranes 620' and 630' at the center via corresponding pins 660' and 670' in order to assist with assembly of the accommodating cell and also to maintain the accommodating cell shape integrity for both membranes 620' and 630'.

The sub-elements 690' and 700' are separated by substantially thinner material portion 570', which is repeated for all other sub-elements outside the central sub-element 680'. These circular material portions are thin enough to provide bending of the sub-elements in case of certain level of difference in pressure between the chambers 640' and 650'. Another side of the sub-elements indicated as 580' for sub-element 690' as the same as for others is also thinner than the rest of each sub-element thickness to assist with each sub-element bending.

The separation between the sub-elements and membrane 630' is of width H' limiting the maximum bending of all sub-elements. The same construction is applied to all other sub-elements. Thus, bending of each sub-element is restricted towards the chamber 650' by the maximum dimension H' which is somewhere in the range of few microns to about 20 microns, depending upon the material refractive indices of the accommodating element and external medium and targeted power difference between far and near vision.

All sub-elements have circular shapes around the optical axis 590'. Though the chamber 640' is shown in the cross-section as being divided by the sub-elements into sub-chambers, all these sub-chambers are connected with each other by the radial channels.

FIG. 7 demonstrates a cross-section of the accommodating cell 600' with optical axis 590' in the stressed state when the ciliary muscle is contracted. As a pressure in the chamber 650' increases, the sub-elements 690', 700', 710' and so on bend at the thinnest places 720' and so on to create surface relief structure of the diffractive surface of the accommodating element 610'. The maximum bending is limited to the magnitude H' which is the width of the chamber 650' resulting in the equivalent groove height or blaze material thickness to produce the Kinoform, i.e. to direct most of the available light in the direction of (−1)-order diffraction for near vision.

The accommodating element 610' between the chambers 640' and 650' takes a shape of surface relief of, more specifically, shape of blazes to form diffractive grooves 740', 750', 760' and so on facing the chamber 650 connected with external medium. The diffractive surface relief heights (blaze material thickness) is restricted by the geometry H' of the accommodating cell to create the Kinoform with the focus for near vision, i.e. 100% of light or most of the available light is directed to (−1)-order diffraction by the created diffractive surface relief surface of the accommodating element 600'.

The surface relief structure of the Accommodating element 610' is constructed to produce the same single focus by all its sub-elements in stressed condition of ocular implants and spectacle lens in order to maximize the image quality. In case of a spectacle lens application where eye rotates and viewing through different portions of the spectacle lens, there is a benefit to divide the accommodating element into zones with different periods of surface relief structures of the zones. Under a stressed condition, the surface relief structure in each zone direct light to different foci of each zone (−1)-order diffraction. Thus, one zone may be for near focus and another zone is for intermediate focus and both foci come into play simultaneously under stressed condition.

Figure 8:
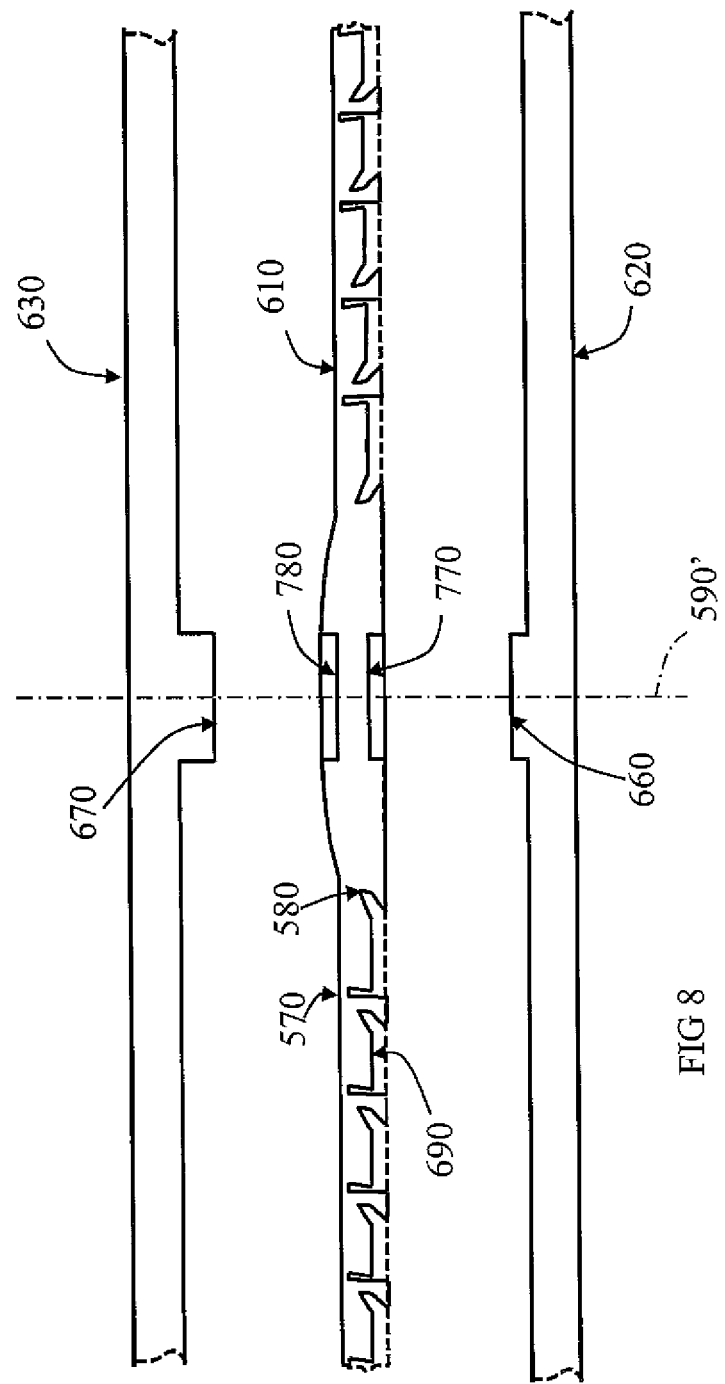
FIG. 8 demonstrates an assembly of the accommodating cell consisting of three elements: front and back membranes to form external walls of the corresponding chambers filled with optical fluids and accommodating element forming the wall between the chambers. The membrane is shown as flat surfaces but can be curved to provide refractive powers. The construction of the accommodating element can be made with diffractive surface of 1-order diffraction for far vision and refractive surface for near vision or even as switching between surface reliefs of different heights to redirect light to the corresponding different orders diffraction.

FIG. 8 demonstrates assembly of the accommodating cell 600 of the FIG. 4 consisting of three elements: front and back membranes 620 and 630 to form external walls of the chambers filled with optical fluids and accommodating element 610 forming the wall between the chambers.

The accommodating element 610 consists of accommodating sub-elements; one sub-element 690 is pointed to on the FIG. 8. Each sub-element includes very thin portion 570 between the sub-elements and thin portion 580 at the opposite side of the sub-element to assist with its bending. It also may include guides 770 and 780 for pins 660 and 670 to assist with the assembly and to maintain shape integrity of the membranes 620 and 640 during accommodating cell actions.

The elements of the accommodating cell can be made of commonly used in ocular applications polymers and particularly elastomers (silicone, acrylic or within the variety of other materials).

The smallest features of the most delicate accommodating element of the accommodating cell is in microns and can be accurately and inexpensively reproduced by vacuum casting or injection molding techniques. In addition, coating can be applied if the elements of the accommodating cell are too thin to prevent permeability by optical fluids, for instance, atomic layer of silver coating which is too thin to interfere with the light transmittance.

FIG. 9 illustrates front view of one of the embodiments of typical configuration of intraocular lens 410 with optical axis 790 of lens optic with the optic center O, with the peripheral optical edge 880, haptics or supporting elements 830 and 840 and the addition of the connecting flexible element 820 attached to the accommodating cell 600 situated inside the intraocular lens 410 of this embodiment and shown by its peripheral edge 900. Optical center "O" is a cross-section of the optical axis 790 with the lens surface. This definition of the optical center is used throughout this invention disclosure. The back element of the lens 410 shown by the peripheral optic edge 880 may include peripheral wedge 890 for attaching the front element shown by its peripheral edge 910 with accommodating cell situated between these two elements.

The connecting element 820 is to connect the accommodating cell 600 that changes the optical state between far and near vision with the sensor cell that interacts with the ciliary muscle to transfer the force resulted from the ciliary muscle contraction and relaxation into a difference in pressure between the chambers of the accommodating cell. The length of the connecting element 820 is about 6 mm which is adequate to connect sensor cell situated at the location of the ciliary tendon of the ciliary muscle and accommodating cell situated inside an intraocular lens.

Upon implantation of lens 410, sensor cell and connecting then by the connecting element 820, there is a period of stabilization when the wound heals and capsule bag undergoes possible fibrosis and shrinkage that may cause uncontrolled pressure on the implant 410 shifting imaging from far to near focus. In order to maintain far vision during this period, a stabilizing chamber 825 can be part of the implant construction which tightens the connecting element 820 to prevent a flow of optical fluids in and from chambers of accommodating cell 600. The stabilizing chamber 825 is filled with BSS by high enough pressure. The original state of the accommodating cell 600 set for far vision is then maintained because the optical fluids are uncompressible.

After the stabilization period when the capsular bag becomes relaxed, the stabilizing chamber 825 is pierced with Nd:YAG laser to release BSS and open up the connecting element 820 to allow optical fluids flow between the accommodating cell 600 and sensor cell.

This principle to use stabilizing chamber with BSS or any other physiologically neutral solution to maintain a desirable optical state by the accommodating implant designed with microfluidic that can be pierced by a laser beam to restore the implant's dynamic state, can be applied to any accommodating design that includes microfluidic action.

FIG. 10 shows the cross-section of the intraocular lens 410 with optical axis 790 as shown on the FIG. 7. It shows also one of the haptics 840. The FIG. 10 demonstrates the accommodating cell 600 situated inside the intraocular lens 410 with connecting element 820 attached to it at one end 930 and the other end 870 of the connecting element is attached to the opposite edge of the intraocular lens optic for its temporary fixation during lens implantation inside the eye. This end 870 is separated from the intraocular lens inside the eye for connection to the sensor cell.

The FIG. 8 demonstrates the stabilizing element 825 blocking the connecting element 820 to prevent optical fluids to flow in and out of the accommodating cell 600 in order to maintain far vision during stabilizing period.

The lens 410 consists of front elements 800 with the front surface 850 and back element 810 with the back surface 860. The front element 800 may be attached to the back element 810 via the wedge mechanism 920 as an inexpensive assembly of the whole lens 410.

FIG. 11 illustrates assembly of the intraocular lens 410 shown on the FIGS. 9 and 10. The intraocular lens of this particular embodiment consists of three elements: front element 800 which can be attached to the back element 810 at the front wedge 920 and the accommodating cell 600 placed between them. Simplest plano-convex shape of the front element enables making an inexpensive variation of its optical characteristics, such as a variety of dioptric powers, asphericity and toricity for astigmatism correction, by shaping the front surface 850. Back element 810 of this embodiment incorporates also haptics 830 and 840 and is of a more complex shape and is less variable element of the intraocular lens manufacturing. Accommodating cell 600 is situated in the hollow at the front of the back element 810 in contact with surface 950 and is secured inside the lens 410 by front element 800 to allow the overall intraocular lens 410 to take a conventional shape of a typical non-accommodating lens and, therefore, to utilize convention implantation techniques.

The connecting element 820 is permanently attached to the accommodating cell at 930 and secured to the lens 410 at the opposite end 870 for the lens 410 implantation and then the end 870 is attached to the sensor cell.

FIG. 12 illustrates the connection between sensor cell 605 and accommodating cell 600. The connecting element 820 is about 6 mm in length which is adequate to place the sensor cell at the proximity of the ciliary muscle for the interaction and accommodating cell to be situated inside the Diffractive Accommodating Lens of this invention.

A dual chamber sensor cell 605 per this example consists of two plates 360 and 370 with chambers 980 or 1010 inside of each plate connected with the corresponding chambers 640 or 650 of the accommodating cell 600. The plates 360 and 370 of the sensor cell 605 are placed externally and internally to the ciliary muscle fibers with the ciliary tendon situated in between to create a differential pressure between the chambers 980 and 1010 of the sensor cell 605 with muscle contraction and relaxation. Pressure at the internal to the muscle chamber 1010 in the plate 370 increases and external to the muscle chamber 980 at the plate 360 reduces with the muscle contraction when the ciliary muscle moves inward and the pressure in the chambers 360 and 370 returns back to the initial state with ciliary muscle relaxation.

Each plate 360 or 370 has hard exterior shell 960 or 990 and soft interior membrane 970 or 1000 to respond to the force exerted by the ciliary muscle and then to transfer the difference in pressure between the sensor cell chambers 980 and 1010 to the difference in pressure between the accommodating cell chambers 640 and 650 via the channels 1020 and 1030 of the connecting element 820.

The corresponding change in pressure between the chambers 640 and 650 of the accommodating cell 600 switches the optical states of the eye between far vision with ciliary muscle relaxation and near vision with ciliary muscle contraction. The pressure threshold is set at the sensor cell 605 between these two corresponding levels of pressure for a reliable change in states of the accommodating cell between far and near vision.

FIG. 13 illustrates some specifies of the dual chamber sensor cell 605 exterior views facing outside the eye, i.e. front view of the plate 360 with the chamber 980 inside. The other chamber 1010 is in the internal plate 370. The exterior of the sensor cell 605 is shown with two ports 1040 and 1050 each connected to each chamber 980 or 1010 to allow in-vivo pressure adjustment between the chambers of the sensor cell after the installation of the sensor cell, Diffractive Accommodating Lens and their connecting after the surgery. This is in order to adjust for a proper pressure threshold between the chambers 640 and 650 of the accommodating cell to reliably switching between the optical states of far and near vision with contraction and relaxation of the ciliary muscle of the patient. The adjustment might be beneficial due to individual variation in ciliary muscle action and sensor cell positions.

The sensor cell can be of different shape and construction and have one chamber with the fluid to interact with the ciliary muscle contraction to transfer the resulted force to the accommodating cell to switch from far to near vision.

FIG. 14 demonstrates aphakic Diffractive Accommodating Lens 410 of this invention which replaces the natural crystalline lens and consisting of optic 400 and haptics 420. The DAL 410 is shown as being placed inside the capsular bag 290. The FIG. 14 demonstrates the placement of the sensor cell with external plate 360 and internal plate 370 around the anterior tendon of the ciliary muscle that includes scleral spur 370. The sensor cell is placed with the exterior plate 360 with its the exterior chamber being exterior to the ciliary muscle 110, 120, 130 and the interior plate 370 with its interior chamber to the interior to the ciliary muscle 110, 120, 130. The FIG. 14 demonstrates two paths of the connecting element 430 between the sensor cell and accommodating cell: through the ciliary sulcus 220 posterior to the iris 180 or iridocorneal angle 280 anterior of the iris 180, path 440. Later will involve an iridotomy by making a puncture-like opening through the iris without the removal of iris tissue for the connecting element to go through the iris 180. The advantage of iridocorneal angle path 440 is that it is more similar to the already developed glaucoma surgery technique that involves a glaucoma shunt installation.

FIG. 15 demonstrates Diffractive Accommodating Lens (DAL) 460 of this invention which compliments a previously installed aphakic convention IOL 450. The DAL 460 includes haptics 470 placed in the commonly used position at the ciliary sulcus 220 in front of the previously implanted conventional IOL 450. The sensor cell with plates 360 and 370 is similar to those described in the FIG. 14. The connection 430 of the sensor cell and DAC 460 is also may have two paths, one through the ciliary sulcus 220 and another through iridocorneal angle 280 to the DAL 460 and are similar to those described in the FIG. 14.

FIG. 16 demonstrates phakic Diffractive Accommodating Lens (DAL) 500 of this invention that does not involved a removal of a natural crystalline lens 190. The DAL 500 is shown as being placed with its haptics 510 in the iridocorneal angle 280 but the phakic DAL can also be iris fixated, i.e. the lens haptics are attached to the iris 180, or phakic DAC can be placed behind the iris 180 and in front of the crystalline lens 190. The sensor cell with plates 360 and 370 is similar to those described in the FIG. 14. The sensor cell and its connection element 520 through the iridocorneal angle 280 with the DAC 500 is similar as one described in the FIG. 14.

FIG. 17 demonstrates corneal implant Diffractive Accommodating Lens (DAL) 530 of this invention which is placed in the cornea 240. The DAL 530 of appropriate shape to match the corneal shape and thickness is placed in the cornea 240 and connected to the sensor cell with plates 360 and 370 is similar to those described in the FIG. 14. The DAL 530 is connected with sensor cell with connection element 540 that goes over the cornea 240. The procedure does not require a penetration inside the eye.

FIG. 18 illustrates another option of the aphakic diffractive accommodating lens 1100 operation that changes its optical states between far and near vision by direct effect of the vitreous pressure or capsular bag tension. As a secondary accommodating effect, ciliary muscle contraction changes choroid tension thus increases vitreous pressure causing crystalline lens-zonule complex to move forward. The effect is also observed with the crystalline lens replacement by aphakic IOL which can move by about 0.1-0.2 mm either forward or even in some instances, backward. Due to diffractive design of the diffractive accommodating lens, a direction of movement is irrelevant as long as there is a change in vitreous pressure and the pressure threshold of the accommodating cell is set within the range of the vitreous pressure variation.

The DAL 1100 consists of front element 1110, back element 1140 and accommodating cell 1160 between them. Front element 1110 incorporates supporting members or haptics 1120 and 1130 to secure lens 1100 position inside the eye. Back element 1140 is attached to the front element 1110 via sub-chambers 1190, 1200, 1210 and 1220 (could be a different sub-chamber design) connected with the accommodating cell 1160 chamber with optical fluid of non-matching refractive index, optically active chamber, with accommodating element material to allow fluid to travel between them. The other optically transparent chamber with matching refractive index is connected with sub-chamber 1180 supported by a flexible membrane to allow its volume to change if the optical fluid is squeezed out from the connecting chamber of the accommodating cell by the pressure from the sub-elements 1190 etc., due to external forces such from the vitreous, for instance. The pressure might be required to be adjusted for relaxed state post-operatively after the healing and lens stabilization inside the capsular bag. This might be performed through a chamber port using a needle.

A DAL may only include optically transparent chamber and function of optically active chamber is taken by the aqueous humour. In this case accommodating element is facing the aqueous humour one side and optically transparent chamber on another.

FIG. 19 demonstrates a cross-section of the diffractive accommodating lens 1100 of the FIG. 18. The lens consists of front element 1110 that includes haptic with one haptic 1130 shown on the FIG. 19. Back element 1140 is held onto the front element 1110 by the wedge structure 1170 and attached to the front element 1110 via sub-chambers 1190 and 1200. These sub-chambers can be of different number and shape.

Vitreous pressure shown by 1239 is exerted on the back element 1140 with variable magnitudes depending on the ciliary muscle contraction and relaxation as well as the lens 1100 fixation inside the eye. This in turn, changes the pressure on the sub-elements 1190, 1200 and others, transferring small amount of the optical fluid into the accommodating cell 1160 chamber with non-matching refractive index. This in turn changes the shape of the surface relief of the accommodating element facing non-matching refractive index chamber by transferring a small amount of optical fluid from the matching refractive index chamber into the corresponding sub-chamber 1180 by flexing its membrane. Sub-chamber 1180 is shown as a ring structure around the accommodating cell external edge but it can be of a different shape and location with maintaining the principle of operation of changing accommodating element surface shape from refractive to diffractive or between orders of diffraction to redirecting light between far and near foci.

The ophthalmic lens described by the FIG. 19 can be substantially simplified with the use of the accommodating cell 600' described by FIGS. 6 and 7. The sub-chambers 1190 and so on are replaced by sub-chambers connected to the optically transparent chamber (OTC) filled with optical fluid of matching refractive index with accommodating element and the optically active chamber is connected to the exterior medium such as aqueous humour. The amount of fluid transfer from sub-chambers to OTC may control the bending of the accommodating elements that creates surface relief structure. No need for sub-chambers 1180 and so on connected with the optically active chamber of the accommodating cell.

Upon implantation the lens 1100 into the capsular bag, there is a few months period when the capsular bag may shrink and change tension on the lens 1100 impacting its relaxed state for far vision. One option to handle this period is to include so called, stabilizing sub-chamber 1185 shown as narrow circular shape in this case separating the front 1110 and back 1140 elements and filled with BSS, for instance. The stabilizing sub-chamber 1185 maintains stability of the lens 1100 during this initial post-operative period by preventing a dynamic change in the optical state until the ocular condition becomes stable. Patient maintains normal Far vision equivalent to any conventional monofocal lens during this period. After the ocular condition is stabilized, the stabilizing sub-chamber 1185 is punctured with a Nd:YAG laser beam, for instance, allowing BSS to be removed into aqueous thus reversing the lens 1100 to the dynamic condition to enabling it to change between relaxed state for Far vision and stressed states for Near vision with absence and presence of accommodating force. Only a small amount of optical fluid, small fraction of milliliter, is transferred in and from the corresponding chambers that involved in changing the shape of the accommodating surface that separates both chambers of the accommodating cell 1160 and switches between far and near vision. The process does not rely on a lens forward movement as with other accommodating IOLs but only on a pressure change required for material transfer in the chambers but only requires that back element 1140 and front element 1110 are squeezed together by about 10-20 microns by the action of ciliary muscle, choroid and vitreous. The lens 1100 itself may move forward or backward during this process which is likely not to exceed a small fraction of millimeter.

The sub-chambers 1200 the diffractive accommodating lens may have transferred to the sensor cell installed to interact with the ciliary muscle directly. In this case, the sensor cell has only one chamber with the fluid and some function of the other chamber described above is taken by the sub-chamber 1180.

If the diffraction accommodating lens design relies on changes of the capsular bag tension, then the construction of the accommodating cell must be different from 600 or 1160 above by providing near vision at the resting state of the capsular bag and far vision at the increased tension of the capsular bag.

The diffractive accommodating lens can be also applied to dual-lens system, U.S. Pat. No. 7,452,378 that relies on the capsular bag action to change optical states between far and near vision. In this case, the accommodating element is to provide far vision in stressed state and near vision in relaxed state to follow the capsular bag actions which is accomplished by either to have diffractive surface with (−1)-order diffraction at relaxed state (near vision) and refractive optic in stressed state (far vision), or refractive optic in the relaxed state (near vision) and diffractive surface with (+1)-order diffraction in stressed state (far vision).

FIG. 20 provides a Longitudinal Spherical Aberration at Far image formed by the Diffractive Accommodating Lenses DAL 1 and DAL 2 per the specifications listed in the Tables 1 and 2 as being examples of the invention.

TABLE 1

Eye model specifications where Diffractive Accommodating Lenses 1 and 2 were analyzed.

| Optical Characteristics Cornea: | Dimension in mm; refractive index |
|---|---|
| Anterior surface radius | 7.8 |
| Refractive index | 1.377 |
| Conic constant (asphericity Q) | Nominal Q = −0.26 |
| Posterior surface radius (mm) | 6.5 |
| Central thickness (mm) | 0.55 |
| Aperture stop or pupil position from posterior corneal surface (mm) | 3.55 |
| Aqueous refractive index | 1.3374 |
| Vitreous refractive index | 1.336 |

TABLE 2

Overall Specifications of Diffractive Accommodating Lens 1 and 2.

| Optical Characteristics | Dimension in mm; refractive index |
|---|---|
| Power (D) | 21.0 |
| Front element | |
| front surface vertex radius | 17.55; bi-sign aspheric(*) |
| material | Acrylic, 1.489 |
| thickness | 0.30 |
| back surface radius | flat |
| Accommodating Cell | |
| plano-parallel plate | Acrylic, 1.489; 0.1 mm thick |
| Chamber A-E | Optical fluid, 1.433 |
| Switchable Element (SE) | Silicone, 1.433; 0.1 mm thick |
| Chamber A-I | Optical fluid, 1.403; 0.05 mm thick |
| plano-parallel plate | Acrylic, 1.489; 0.1 mm thick |
| Back element | |
| front surface radius | flat |
| material | Acrylic, 1.489 |
| thickness | 0.60 |
| back surface radius | −8.01 |

(*)Bi-sign aspheric has been disclosed by Portney in U.S. patent application No.: 12/415,742. Aspheric coefficients of the front surface referenced to in the Table 2 are: −0.0015 at $r^4$, 0.000172 at $r^6$, 0.00000446 at $r^8$ and 0.000006 at $r^{10}$.

The LSAs of Far images of DAL 1 and DAL 2 are the same because the refractive specifications of both lenses are the same. The LSA demonstrates positive spherical aberration for up to about 1 mm from the lens center and negative spherical aberration outside 1 mm distance which is the characteristic of bi-sign asphericity.

The surface for far vision can be also made with a power variation to increase depth of focus at far. For instance, to have higher power at the center and then progressively reduced power to create negative power slop known as increasing depth of focus. The power progressive may be up to 1 D with only marginal impact on image quality but to reduce sensitivity to residual refractive error.

FIG. 21 and FIG. 22 provide Longitudinal Spherical Aberrations at Near images by the Diffractive Accommodating Lenses DAL 1 and DAL 2 produced at (−1)-order diffraction per the specifications of Eye model, Diffractive Accommodating Lenses 1 and 2 provided in the Tables 1 and 2. The surface of the accommodating element facing OAC acting as imaging zone that switches between far and near vision is placed within about 4 mm diameter as shown on the Table 3 below. The LSA graphs show near LSA within this diameter and portion of far LSA outside 4 mm diameter as the LSA graphs is shown for 5 mm diameter on the FIGS. 19 and 20 and thus capturing some of far LSA close to 5 mm diameter (2.5 mm distance from the lens optical center), DAL 1 includes only small amount of spherical aberration in the (−1) order diffraction to produce close to spherical wavefront in creating near retinal image at 36 cm of near viewing distance. DAL 2 includes a significant amount of spherical aberration in the (−1)-order diffraction to create retinal image from a near object placed not only around 36 cm viewing distance as in DAL 1 but at up to about 27 cm of near viewing distance, i.e. to offer the increased depth of focus at near of about 1 D. The increase in depth of focus at near is demonstrated by the corresponding LSA shape on the FIG. 20 which starts at more near focus at the lens center and gradually shifts farther away to create a negative slope of the power graph. The extension of the range of vision towards closer near is beneficial as there is a natural tendency to bring a near material closer to the eyes to observe finer details. The increased depth of focus of about 1 D at near may be shifted to intermediate vision by providing a range of vision from about 50 cm at intermediate to 36 cm at near. This is to expend the effectiveness of the diffractive accommodating lens from far and near to include intermediate vision.

Specifications of the diffractive surfaces of the Accommodating cells with small amount of spherical aberration for near image (DAL 1) and large amount of spherical aberration to extend depth of focus at image by (−1)-order diffraction (DAL 2) are provided in the Table 3.

Diffractive Accommodating Lens DAL 1 changes between two distinct foci of Far image demonstrated by far LSA in the FIG. 18 and Near image demonstrated by near LSA in the FIG. 21. Depth of focus or progressive foci feature at near can be increased as shown in DAL 2 by modification of the phase coefficients for (−1) order diffraction to include spherical aberration that spreads light along the optical axis at the near image either to improve near close up or improve intermediate vision capability in addition to near. This extension of depth of focus at (−1)-order diffraction is accomplished independently of the Far image LSA.

Another option to introduce multiple foci (near and intermediate) in stressed condition is to use multi-zone option, i.e. to divide the accommodating element into zones that under stress condition produce surface relief of different periodic structure resulting in different foci of (−1)-order diffraction of each zone. This way one zone, central for instance, may manifest intermediate focus and peripheral annulus zone to provide near foci or vice versa. Similar multi-zonal option can be also applied to the switchable diffractive surface that is based on the refractive index change where zones have different refractive index amplitudes.

The near focus of DAL 1 and DAL2 can be in the range that corresponds to intermediate vision and for generality the meaning of near focus referenced in this invention also includes intermediate focus, i.e. any focus produced by the accommodating cell in stressed state over the far focus produced in the relaxed state.

The result of the depth of focus increase at (−1)-order of diffraction for DAL 2 involves the change in the diffraction grooves shape which is illustrated by the difference in groove

TABLE 3

Specification of the near diffractive state of (−1)-order diffraction of the Accommodating cells of the Diffractive Accommodating Lens DAL 1 and DAL 2.

| Per materials specified of Table 2 the diffractive grooves heights (blaze material thickness) are constant | H = 0.0183 mm to create Kinoform in compressed state of the Accommodating Cell |
|---|---|

| | Phase coefficients (radians) $\alpha_i$ of the Phase Function $\Phi_{-1}(r_i)$ per Eq. 3 | | | |
|---|---|---|---|---|
| | r | $r^2$ | $r^4$ | $r^6$ |
| DAL 1 (small spherical aberration) | 0.231 | 20.968 | 1.116 | −0.23 |
| DAL 2 (large spherical aberration) | 0.168 | 31.867 | −4.215 | 0.340 |

| | Groove radii (mm) | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| DAL 1 | 0.538 | 0.738 | 0.925 | 1.065 | 1.187 | 1.298 | 1.400 | 1.496 | 1.586 | 1.673 | 1.758 | 1.841 | 1.923 |
| DAL 2 | 0.447 | 0.642 | 0.799 | 0.937 | 1.065 | 1.187 | 1.305 | 1.422 | 1.537 | 1.653 | 1.768 | 1.881 | 1.981 |

The groove height H is to provide 100% diffraction efficiency for (−1)-order diffraction or at least to direct most of the available light to near focus, i.e. the Diffraction Accommodating Lens in the corresponding diffractive state becomes the Kinoform. If groove height is only a fraction of H because a difference in pressure between the chambers is below the threshold, the DAL becomes a multifocal diffractive lens that split light between Far and Near foci. The corresponding vision is only for near because of the presence of some accommodating force which only occurs for near vision. It takes only to achieve 40% of H for a grooves height (maximum height for Kinoform) in order to direct 30% of light to Near focus and achieve sufficient near vision. In case of the example on the table 3, it takes 7 microns or more of grooves height to direct 30% or more of total light to Near focus.

radii between DAL 1 and DAL2. The grooves radii of DAL 1 with small amount of spherical aberration is practically equivalent the grooves radii defined by the paraxial approximation of the Equation 1. Both DAL 1 and 2 include 13 grooves within about 4 mm diameter with central two grooves radii DAL 2 being substantially smaller the corresponding grooves in DAL 1 and also by the radius of a more peripheral groove of DAL 2 reaching a similar magnitude as the radius of the same groove order in DAL1, on 11th groove in the Table 3 of this example. Substantially smaller in general means about 10% of more smaller. Substantially similar usually means within ±10%. The radii of further grooves of DAL 2 then may exceed the radii of the corresponding grooves of DAL 1. This comparison between the grooves of any diffractive lenses that produces small amount of spherical wavefront (DAL 1) with the radii defined by the paraxial form of the Equation 1 and wavefront with extended spherical aberration that increased depth of focus (DAL 2) is applied to the same orders of diffraction and the same image positions defined by the diffraction order focal length.

In case of an annular zone with progressive foci feature, the radii of central grooves reference to the grooves starting at the internal side of the annular zone, i.e. a reference to "central grooves" includes central grooves of a zone that includes optical center of the lens or an annular zone.

Similar phase coefficients modification to enhance depth of focus at near can be applied to monofocal diffractive non-accommodating lens, multifocal diffractive optics where light is split between far and near foci and near image is formed, for example, by (−1)-order diffraction and switchable diffractive surface that is based on the change in the refractive index modulation. Appropriate phase coefficients can be applied to the multifocal diffractive optic, for instance, to lead to similar diffractive grooves shape change from the one producing spherical wavefront to result in the increase in depth of focus for (−1)-order diffraction. The result will be the same correlation between the diffractive grooves as those in comparing DAL 1 as defined by the paraxial form of the Equation 1 and DAL 2 in the Table 3.

The difference between a DAL and corresponding multi-focal optic would be grooves height or blaze material thickness in case of blaze grooves: the grooves heights in multifocal optic is to split light between far and near images and in DAL is to direct most of the available light to the diffractive focus.

Spherical aberration of Far image can also be expended to enhance depth of focus at far towards intermediate independently of the near image depth of focus extension. This can be accomplished by modifying at least one of the refractive surfaces of the Diffractive Accommodating Lens including the refractive surface of the Accommodating Cell formed in the state of Far vision shown in this particular embodiment.

FIG. 23 and FIG. 24 illustrate diffractive accommodating lens for spectacles. Almost universally, the series of front surface base curves to cover the entire spectacles prescription range is used. This system reduces lens inventory and eliminates the need for a different base curve for every possible prescription. Sets of semi-finished blanks, with front curves varying in steps, are stocked in local optical laboratories, and charts or computer programs show laboratory personnel which blank should be used for each prescription. The system was developed from the ability to have spectacle lens bending (combination of front and back surface curvatures) that limits power error and oblique astigmatism error with eye rotation and viewing through different area of the spectacle lens. Eye rotation is usually up to 30 degrees or even 40 degrees from the optical axis on each side of the spectacle lens optical center.

The disclosed Diffractive Accommodating Lens for spectacles 1300 is built around the same system of front base curves by adding Accommodating Cell described above and shaped it similarly to the base surface onto the front base surface of the single vision spectacle lens, 1310 and 1320. This is one of the embodiments but the design is not limited to this particular description as the accommodating cell may be either add-on or as the insert. The back surface of the lens may include spherical and tone surface equivalent to single focus prescription of the same wearer of the glasses.

The Accommodating Cell of the Diffractive Accommodating Lens may include two chambers OTC and OAC or only one chamber OTC if the surface relief structure of the Accommodating Element faces the air which acts as OAC. In later case it is desirable for the surface relief structure to face the base surface for its protection. The front membrane of the Accommodating Cell facing the exterior of the lens can be made thick enough to maintain Accommodating Cell integrity during lens cleaning.

The chambers of the Accommodating Element are connected to the control mechanism 1340 consisting of two chambers each connected to the corresponding chamber of the Accommodating Cell and separated by the moving separator connected to the nub 1350. The nub 1350 can be moved be the wearer from one end to another to push the optical fluid in the control mechanism 1340 in and out of the corresponding Accommodating Cell chambers in order to change Accommodating Cell states between far and near vision. The mechanism arrangement can be more conspicuous by placing it in the skull temple 1370.

The near vision state of the accommodating cell is demonstrated on the FIG. 24 by the non zero height diffractive grooves 1410 and 1420 centered at the near vision centers at both spectacle lenses placed below the corresponding far vision centered 1415 and 1425 which practically coincide with optical centers of the corresponding spectacles lenses. The nub 1350 is shown at its left position for far vision in the FIG. 23 and right position for near vision in the FIG. 24. The Accommodating cell of the lens at the other side of the spectacles 1310 is also connected to the control mechanism 1340 via line 1360 be connecting element as a tube passing through the bridge 1380 and also the nose pad 1390 depending upon the frame construction. This is to allow switching between far and near vision in both spectacle lenses simultaneously.

The diffractive grooves 1400 are optically designed to minimize power and oblique astigmatism errors for near vision with eye rotation within comfortable field of about 15-30 degrees range in different directions from the near vision optical center located at the lower portion of each spectacle lent and closer to the middle of spectacles than the optical center of each lens that considers with far vision center.

The surface relief structure of the Accommodating Cell may have multi-order diffraction where the phase period between the grooves is scaled up by the multiple factors, for instance by factor of 4-6. The benefit of the multi-order diffraction is the reduced chromatic aberration which is particularly importance for spectacle lenses where the control of transverse chromatic aberration raised with eye rotation is important.

The major issue with present day glasses for Presbyopia is the inability to see things that are close or intermediate, but straight ahead. The DAL for spectacles allows addressing this issue by expending the area for far and near vision by switching between different states. The lens also allows addressing intermediate vision in three options:

(A) Trifocal arrangement to use +1-order diffraction for far, zero-order for intermediate and (−1) order for near or superposition of two periodicities of different add powers. There is the ability for precise control of optical fluid in and out of the accommodating cell chamber to switch between not only two but three diffraction orders. For instance, by removing the precise amount of fluid form the OAC, the accommodating element is bent in opposite direction from the previously explained (−1)-order diffraction to produce +1-order diffraction, and also by injecting the precise amount of fluid into the OAC to produce (−1) order diffraction. In this case, the relaxed state would be for intermediate vision.

(B) Another option is to include the near vision with progressive diffractive design as explained by the FIG. 22. In this case, the intermediate power between far and near range covers the center of the lens to allow the wearer to look straight ahead for intermediate, computer screen, for instance.

(C) The third option is to divide the accommodating element into zones of different periodic structures thus the separations between diffraction orders are different between the zones. It means they produce different foci for (−1)-order diffraction as explained by the specifications to the FIG. 5 or 7. Near zone, i.e. zone that produces shorter focal length by its (−1)-order diffraction for near and it is placed at the center of near vision below the optical center of the spectacle lens that concedes with the center for far vision. Peripheral zone, i.e. zone that produces longer focal length by (−1)-order diffraction for intermediate includes optical center of the spectacle lens to allow wearer to look straight ahead onto intermediate object such as a computer screen, for instance. Both zones may take large areas of the spectacle lens to allow for a comfortable field because they replace far power area by switching the accommodating element and not just complimenting the area of far vision as in conventional bifocals, trifocals and progressive glasses.

FIG. 25 illustrates a preferred embodiment of spectacle lens to provide far vision in one optical state and another state is a combination of (B) and (C) options described under the FIGS. 23 and 24 above where the accommodating cell is divided into two zones in the activated optical state, central zone around 1410' and 1420' to produce near focus in stressed condition and peripheral around optical centers 1415' and 1425' of the spectacle lenses to produce intermediate focus. The corresponding multizone structure of different periodic structures of the diffractive grooves creates different foci for (−1)-order diffraction between different zones. The imaginable lines separating the zones are shown as 1430 and 1435 to illustrate the location of near focus zone and intermediate focus zone.

A change in pressure to switch between different states of surface relief periodic structure heights can be accomplished only mechanically with optical fluid transfer to and out of the optical transparent changer but also electronically by changing magnetic or electrical states of the accommodating element and membranes. For instance, changing the magnetic states of the accommodating element and membrane forming the chamber into opposite or the same polarities would increase or reduce pressure between the accommodating element and the membrane forcing the accommodating element to change the surface relief structure height and, therefore, redirecting light from one diffractive order to another (including zero order created by refractive surface).

The intermediate annular zone includes progressive foci change as shown under FIG. 22 in reference to DAL 2 but for the annular zone. This progressive change in foci is from intermediate at 1415' and 1425' with foci reduction towards lines 1430 and 1436 to the level of near focus is in order to have a smooth foci transition from the peripheral intermediate vision zone and central near vision zone of the accommodating cell thus avoiding an image jump common with abrupt foci change when the eye moves through this abrupt focus change. The peripheral zones of the intermediate focus of the accommodating cells of left and right spectacles lenses includes corresponding optical centers 1415' and 1425' to allow the wearer to look onto intermediate object straight ahead without tilting the head or training eyes to look through a specific area of the spectacle lens.

Multizone structure of different periodic structures of the diffractive grooves that results in different foci for (−1)-order diffraction between different zones can be further expanded to be used as indicator of the optical state of the spectacles. Additional zone is placed at the right periphery of right spectacle lens and left periphery of the left spectacle lens. The surface relief periodic structure for (−1)-order diffraction of this third zone has substantially smaller periods than near zone thus producing focus that is out of focus from retinal imaging. Therefore, the corresponding zone does not produce imaging for object at any distance, it effectively reduces the field of the spectacle lens in horizontal plane. This can be used as an indicator to the wearer in watt state his or her spectacles are—in relaxed state for far vision or stressed state for near vision.

The principle of multizone structure that includes different zones of periodic structure of the diffractive grooves producing different foci for (−1)-order diffraction at different zones manifested in stressed state may be applied to the spectacle lens with refractive index modulation as the improvement over the switchable lens described by Li and his colleagues and referenced to above. In this case the spectacle lens includes zones of different refractive index amplitudes. For instance, the spectacle lens produce far vision with refractive surface and near vision with non-zero diffractive order created by refractive index modulation from the original refractive surface and the diffractive surface is divided into at least two zones of different periodic structure to produce different focus positions for the same non-zero diffractive order simultaneously such as near and intermediate foci. The improvement may also include a foci transition between intermediate vision zone and near vision zone to avoid image jump.

System for automated switching between far and near vision can be also added to the Diffractive Accommodating Lens by including gaze distance detection. Gaze distance detection includes a combination of emitter-sensors for infrared radiation placed at the spectacle lens or spectacles frame. It is based on the measurement of convergence angle between line of sights of right and left eyes from which the object distance is calculated. The light of sights are measures by detecting the reflection off the corneas or pupil tracking or by more accurate methods such as a comparison of the reflection from front corneal surface with either the pupil position or 4th Purkinje image (reflection from back surface of the eye's lens). One of the emitter-sensors is shown as 1330 and the FIGS. 23 and 24 to demonstrate one of three emitter-sensors per each spectacle right and left sides to apply triangulation.

The signal from the sensors is passed to the microprocessor placed in the skull temple 1370 to calculate the gaze distance to the viewing object. As the distance lies within a near range, the corresponding signal is sent to the electronic control mechanism placed in place of 1340. It can be a micro solenoid acting as toddle switch to move armature that pushes the optical fluid similar to the described above mechanical control mechanism 1340. The manual override might be still included.

FIG. 26 and FIG. 27 demonstrate Diffractive Accommodating Lens application to contact lenses. The design utilizes a principle of bifocal segmented lens where the lens rides up pushed by the lower lid when the wearer looks down to look through the lower near segment of the lens. The lens rides down by its gravity when the wearer looks up to look through the distance segment of the lens. The key point is that the lower lid applies pressure to the lens to ride it up which is used to control switching between far and near vision of the Diffractive Accommodating Lens 1450.

The lens 1450 is facing by front surface 1470 in the FIG. 23 and the Accommodating Cell 1500 is represented by the diffractive grooves 1460. Per the FIG. 26, the chamber 1480 filled with optical fluid is pressured by the lower lid when the wearer looks down. Similar to a segmented lens, the lens 1450 utilized the weighted bevel at the bottom of the lens, 1510 with the chamber 1480 inside it to minimize the lens rotation. The back surface 1490 shape can be maintained similar to one in a typical bifocal segmented lens.

The contact lens can be also constructed with only optically transparent chamber and the air at the front surface of the lens or tear layer at the back surface to function as the optically active chamber. In this case, the front or back surface of the lens changes between refractive shape for far vision and diffractive shape of (−1)-order diffraction for near vision. This simplified construction allows to make the lens as thin as the corresponding segmented single focus lens.

When the wearer looks down, the lens 1450 maintains its position but the pressure from the lower lid transfers small amount of optical fluid to the Optically Transparent Chamber of the Accommodating Cell 1500 of the lens switching it from far to near vision. As the wearer looks up, the pressure on the chamber 1480 is released and the Accommodating Cell 1500 takes the relaxed state for far vision. The benefit over the segmented lens is that there is no need to precise lens fitting for proper riding up and down as the most of lens area is switched between far and near vision thus simplifying the fitting and reducing a likelihood that a wrong segment interferes with the vision.

Although there has been hereinabove described a specific switchable diffractive accommodating lens and method in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An accommodating element for use in an ophthalmic device, said accommodating element comprising:
    a formable element; and
    a plurality of diffractive groove forming channels disposed on one side of said formable element;
a formable surface disposed on an other side of said formable element comprising a variable diffractive groove height in response to a change of pressure differential between the plurality of channels on one side and the formable surface on the other side, thereby changing the amount of light directed to a non-zero order diffractive focus.

2. An ophthalmic device comprising:
    an accommodating element having a formable surface on one side and a plurality of diffractive groove forming channels disposed on the other side of said accommodating element and in an operative relationship with the formable surface for temporarily establishing the formable surface with a non-zero relief structure having a variable height in response to a change of pressure differential applied to the formable surface on the one side and the plurality of diffractive groove forming channels on the other side; and
    an optic combined with said accommodating element, said optic being selected from a group consisting of an intraocular lens, a corneal implant, a spectacle lens, and a contact lens.

3. An ophthalmic device comprising:
    a membrane;
    a flexible accommodating element disposed adjacent to said membrane for creating an optically transparent chamber between said membrane and one side of the flexible accommodating element;
    a plurality of diffractive groove forming channels disposed in said one side of the flexible accommodating element;
    a fluid disposed in said optically transparent chamber between the flexible accommodating element and the membrane within the plurality of diffractive groove forming channels;
    a formable surface on an other side of the flexible accommodating element configured to change shape in relation to a change in a diffractive groove height of the diffractive groove forming channel when subjected to a pressure differential applied to the plurality of diffractive groove forming channels on the one side and the formable surface on the other side, said fluid having a refractive index matching a refractive index of the flexible accommodating element; and
    an optic combined with said accommodating cell, said optic being selected from a group consisting of an intraocular lens, a corneal implant, a spectacle lens, and a contact lens.

4. An ophthalmic device with a switchable diffractive surface, comprising:
    a flexible element comprising a continuous surface on a first side and a plurality of diffractive groove forming channels on a second side opposite the first side, the plurality of diffractive groove forming channels configured to change a diffractive groove height of the continuous surface when subjected to a pressure differential between the first side and second side of the flexible element;
    a first optical fluid adjacent to the continuous surface on the first side of the flexible element comprising a non-matching refractive index in relation to the flexible element; and
    a second optical fluid adjacent to and within the plurality of diffractive groove forming channels on the second side of the flexible element comprising a matching refractive index in relation to the flexible element.

5. The ophthalmic device of claim 4, further including an first optical membrane adjacent to the first optical fluid opposite the first side of the flexible element forming an optically active chamber between the first optical membrane and the flexible element.

6. The ophthalmic device of claim 5, further including an second optical membrane adjacent to the second optical fluid and abutting the second side of the flexible element forming an optically transparent chamber between the second optical membrane and the plurality of diffractive groove forming channels.

* * * * *